(12) United States Patent
Chu et al.

(10) Patent No.: US 7,776,927 B2
(45) Date of Patent: Aug. 17, 2010

(54) EMULSIONS AND TECHNIQUES FOR FORMATION

(75) Inventors: Liang-Yin Chu, Chengdu (CN); Ho Cheung Shum, Hong Kong (CN); Alberto Fernandez-Nieves, Atlanta, GA (US); Andrew S. Utada, Cambridge, MA (US); Enric Santanach Carreras, Cambridge, MA (US); David A. Weitz, Bolton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/058,628

(22) Filed: Mar. 28, 2008

(65) Prior Publication Data

US 2009/0012187 A1 Jan. 8, 2009

Related U.S. Application Data

(60) Provisional application No. 60/920,574, filed on Mar. 28, 2007.

(51) Int. Cl.
*B01F 3/08* (2006.01)
(52) U.S. Cl. .............................. 516/54; 347/55; 428/3; 428/407
(58) Field of Classification Search .................... 516/54
See application file for complete search history.

(56) References Cited

U.S. PATENT DOCUMENTS

| | | | |
|---|---|---|---|
| 3,980,541 A | 9/1976 | Aine | |
| 4,279,345 A | 7/1981 | Allred | |
| 4,508,265 A | 4/1985 | Jido | |
| 4,865,444 A | 9/1989 | Green et al. | |
| 4,931,225 A | 6/1990 | Cheng | |
| 5,204,112 A | 4/1993 | Hope et al. | |
| 5,378,957 A | 1/1995 | Kelly | |
| 5,452,955 A | 9/1995 | Lundstrom | |
| 5,512,131 A | 4/1996 | Kumar et al. | |
| 5,617,997 A | 4/1997 | Kobayashi et al. | |
| 5,681,600 A | 10/1997 | Antinone et al. | |
| 5,762,775 A | 6/1998 | DePaoli et al. | |
| 5,935,331 A | 8/1999 | Naka et al. | |
| 5,942,443 A | 8/1999 | Parce et al. | |
| 5,980,936 A | 11/1999 | Krafft et al. | |
| 6,046,056 A | 4/2000 | Parce et al. | |
| 6,116,516 A | 9/2000 | Ganan-Calvo | |
| 6,119,953 A | 9/2000 | Ganan-Calvo et al. | |
| 6,120,666 A | 9/2000 | Jacobson et al. | |
| 6,149,789 A | 11/2000 | Benecke et al. | |
| 6,150,180 A | 11/2000 | Parce et al. | |
| 6,174,469 B1 | 1/2001 | Ganan-Calvo | |
| 6,187,214 B1 | 2/2001 | Ganan-Calvo | |
| 6,189,803 B1 | 2/2001 | Ganan-Calvo | |
| 6,196,525 B1 | 3/2001 | Ganan-Calvo | |
| 6,197,835 B1 | 3/2001 | Ganan-Calvo | |
| 6,221,654 B1 | 4/2001 | Quake et al. | |
| 6,234,402 B1 | 5/2001 | Ganan-Calvo | |
| 6,241,159 B1 | 6/2001 | Ganan-Calvo et al. | |
| 6,248,378 B1 | 6/2001 | Ganan-Calvo | |
| 6,267,858 B1 | 7/2001 | Parce et al. | |
| 6,274,337 B1 | 8/2001 | Parce et al. | |
| 6,299,145 B1 | 10/2001 | Ganan-Calvo | |
| 6,301,055 B1 | 10/2001 | Legrand et al. | |
| 6,306,659 B1 | 10/2001 | Parce et al. | |
| 6,355,198 B1 | 3/2002 | Kim et al. | |
| 6,357,670 B2 | 3/2002 | Ganan-Calvo | |
| 6,386,463 B1 | 5/2002 | Ganan-Calvo | |
| 6,394,429 B2 | 5/2002 | Ganan-Calvo | |
| 6,399,389 B1 | 6/2002 | Parce et al. | |
| 6,405,936 B1 | 6/2002 | Ganan-Calvo | |
| 6,408,878 B2 | 6/2002 | Unger et al. | |
| 6,429,025 B1 | 8/2002 | Parce et al. | |
| 6,432,148 B1 | 8/2002 | Ganan-Calvo | |
| 6,432,630 B1 | 8/2002 | Blankenstein | |
| 6,450,189 B1 | 9/2002 | Ganan-Calvo | |

(Continued)

FOREIGN PATENT DOCUMENTS

CH 563807 7/1975

(Continued)

OTHER PUBLICATIONS

"Cool Picture of the Moment" (Experimental Soft Condensed Matter Group, Harvard University, retrieved from web site URL:http://www.seas.harvard.edu/projects/weitzlab/coolpic16012007.html, Jan. 16, 2007, IDS document No. XP-002514708).*

Ahn, K., et al., "Dielectrophoretic manipulation of drops for high-speed microfluidic sorting devices," *Applied Physics Letters*, 2006, 88, 024104-1-024104-3.

Ando, S., et al., "PLGA Microspheres Containing Plasmid DNA: Preservation of Supercoiled DNA via Cryopreparation and Carbohydrate Stabilization," *Journal of Pharmaceutical Sciences*, vol. 88, No. 1, pp. 126-130 (1999).

(Continued)

*Primary Examiner*—Ling-Siu Choi
*Assistant Examiner*—Chun-Cheng Wang
(74) *Attorney, Agent, or Firm*—Wolf, Greenfield & Sacks, P.C.

(57) ABSTRACT

The present invention generally relates to emulsions such as multiple emulsions, and to methods and apparatuses for making emulsions, and techniques for using the same. A multiple emulsion generally describes larger droplets that contain one or more smaller droplets therein which, in some cases, can contain even smaller droplets therein, etc. Emulsions, including multiple emulsions can be formed in certain embodiments with generally precise repeatability, and can be tailored to include any number of inner droplets, in any desired nesting arrangement, within a single outer droplet. In addition, in some aspects of the invention, one or more droplets may be controllably released from a surrounding droplet.

20 Claims, 10 Drawing Sheets

U.S. PATENT DOCUMENTS

| | | | |
|---|---|---|---|
| 6,464,886 | B2 | 10/2002 | Ganan-Calvo |
| 6,489,103 | B1 | 12/2002 | Griffiths et al. |
| 6,506,609 | B1 | 1/2003 | Wada et al. |
| 6,508,988 | B1 | 1/2003 | Van Dam et al. |
| 6,540,895 | B1 | 4/2003 | Spence et al. |
| 6,554,202 | B2 | 4/2003 | Ganan-Calvo |
| 6,557,834 | B2 | 5/2003 | Ganan-Calvo |
| 6,558,944 | B1 | 5/2003 | Parce et al. |
| 6,558,960 | B1 | 5/2003 | Parce et al. |
| 6,560,030 | B2 | 5/2003 | Legrand et al. |
| 6,592,821 | B1 | 7/2003 | Wada et al. |
| 6,608,726 | B2 | 8/2003 | Legrand et al. |
| 6,610,499 | B1 | 8/2003 | Fulwyler et al. |
| 6,614,598 | B1 | 9/2003 | Quake et al. |
| 6,630,353 | B1 | 10/2003 | Parce et al. |
| 6,645,432 | B1 | 11/2003 | Anderson et al. |
| 6,660,252 | B2 | 12/2003 | Matathia et al. |
| 6,752,922 | B2 | 6/2004 | Huang et al. |
| 6,790,328 | B2 | 9/2004 | Jacobson et al. |
| 6,806,058 | B2 | 10/2004 | Jesperson et al. |
| 6,890,487 | B1 | 5/2005 | Sklar et al. |
| 6,935,768 | B2 | 8/2005 | Lowe et al. |
| 7,068,874 | B2 | 6/2006 | Wang et al. |
| 7,115,230 | B2 | 10/2006 | Sundararajan et al. |
| 7,268,167 | B2 | 9/2007 | Higuchi et al. |
| 2002/0004532 | A1 | 1/2002 | Matathia et al. |
| 2002/0008028 | A1 | 1/2002 | Jacobson et al. |
| 2002/0119459 | A1 | 8/2002 | Griffiths |
| 2003/0015425 | A1 | 1/2003 | Bohm et al. |
| 2003/0039169 | A1 | 2/2003 | Ehrfeld et al. |
| 2003/0124586 | A1 | 7/2003 | Griffiths et al. |
| 2004/0096515 | A1 | 5/2004 | Bausch et al. |
| 2004/0182712 | A1 | 9/2004 | Basol |
| 2005/0032238 | A1 | 2/2005 | Karp et al. |
| 2005/0032240 | A1 | 2/2005 | Lee et al. |
| 2005/0172476 | A1 | 8/2005 | Stone et al. |
| 2005/0183995 | A1 | 8/2005 | Deshpande et al. |
| 2005/0207940 | A1 | 9/2005 | Butler et al. |
| 2005/0221339 | A1 | 10/2005 | Griffiths et al. |
| 2006/0051329 | A1 | 3/2006 | Lee et al. |
| 2006/0078888 | A1 | 4/2006 | Griffiths et al. |
| 2006/0078893 | A1 | 4/2006 | Griffiths et al. |
| 2006/0108012 | A1 | 5/2006 | Barrow et al. |
| 2006/0163385 | A1 | 7/2006 | Link et al. |
| 2006/0263888 | A1 | 11/2006 | Fritz et al. |
| 2007/0003442 | A1 | 1/2007 | Link et al. |
| 2007/0054119 | A1 | 3/2007 | Garstecki et al. |
| 2007/0056853 | A1 | 3/2007 | Aizenberg et al. |
| 2007/0195127 | A1 | 8/2007 | Ahn et al. |
| 2008/0003142 | A1 | 1/2008 | Link et al. |
| 2009/0012187 | A1 | 1/2009 | Chu et al. |
| 2009/0131543 | A1 | 5/2009 | Weitz et al. |

FOREIGN PATENT DOCUMENTS

| | | |
|---|---|---|
| EP | 0249007 A2 | 12/1987 |
| EP | 1362634 A1 | 11/2003 |
| EP | 1741482 A2 | 1/2007 |
| GB | 1 446 998 | 8/1976 |
| GB | 2433448 A | 6/2007 |
| WO | WO 96/29629 A2 | 3/1996 |
| WO | WO 00/70080 A1 | 11/2000 |
| WO | WO 00/76673 A1 | 12/2000 |
| WO | WO 01/12327 A1 | 2/2001 |
| WO | WO 01/68257 A1 | 9/2001 |
| WO | WO 01/69289 A2 | 9/2001 |
| WO | WO 01/72431 A1 | 10/2001 |
| WO | WO 01/89787 A2 | 11/2001 |
| WO | WO 01/89788 A2 | 11/2001 |
| WO | WO 01/94635 A2 | 12/2001 |
| WO | WO 02/18949 A2 | 3/2002 |
| WO | WO 02/47665 A2 | 6/2002 |
| WO | WO 02/103011 A1 | 12/2002 |
| WO | WO 03/011443 A2 | 2/2003 |
| WO | WO 2004/002627 A2 | 1/2004 |
| WO | WO 2004/002627 A3 | 1/2004 |
| WO | WO 2004/038363 A2 | 5/2004 |
| WO | WO 2004/071638 A2 | 8/2004 |
| WO | WO 2004/091763 A2 | 10/2004 |
| WO | WO 2005/002730 A1 | 1/2005 |
| WO | WO 2005/021151 A1 | 3/2005 |
| WO | WO 2005/049787 A2 | 6/2005 |
| WO | WO 2005/103106 A1 | 11/2005 |
| WO | WO 2006/002641 A1 | 1/2006 |
| WO | WO 2006/078841 A1 | 7/2006 |
| WO | WO 2006/096571 A | 9/2006 |
| WO | WO 2006/096571 A2 | 9/2006 |
| WO | WO 2006/101851 A2 | 9/2006 |
| WO | WO 2006096571 A2 * | 9/2006 |
| WO | WO 2007/081385 A2 | 7/2007 |
| WO | WO 2007/089541 | 8/2007 |
| WO | WO 2008/121342 A2 | 10/2008 |

OTHER PUBLICATIONS

Anna, S.L., et al., "Formation of dispersions using "flow focusing" in microchannels," *Applied Physics Letters*, vol. 82, No. 3, pp. 364-366 (2003).

Benichou, A., et al., "Double Emulsions Stabilized by New Molecular Recognition Hybrids of Natural Polymers," *Polym. Adv. Tehcnol.*, vol. 13, pp. 1019-1031 (2002).

Bibette, J., et al., "Emulsions: basic principles", Rep. Prog. Phys.. 62 (1999) 969-1033.

Chao, W., et al., "Control of Concentration and Volume Gradients in Microfluidic Droplet Arrays for Protein Crystallization Screening", $26^{th}$ Annual International Conference of the IEEE Engineering in Medicine and Biology Society, Sep. 1-5, 2004, Francisco, California.

Chao, W., et al., "Droplet Arrays in Microfluidic Channels for Combinatorial Screening Assays", Hilton Head 2004: A Solid State Sensor, Actuator and Microsystems Workshop, Hilton Head Island, South Carolina, Jun. 6-10, 2004.

Chen, C.C., et al., "Microfluidic Switch for Embryo and Cell Sorting," The $12^{th}$ International Conference on Solid State Sensors, Actuators, and Microsystems, Boston, MA Jun. 8-12, 2003 *Transducers*, vol. 1, pp. 659-662 (2003).

Chen, L.X., et al., "Capturing a Photoexcited Molecular Structure Through Time-Domain X-ray Absorption Fine Structure," Science, vol. 292, pp. 262-264 (2001).

Cheng, Z., et al., "Electro flow focusing in microfluidic devices," Microfluidics Poster, presented at DEAS, "Frontiers in Nanoscience," presented Apr. 10, 2003.

Chiba, M., et al., "Controlled protein delivery from biodegradable tyrosine-containing poly(anhydride-co-imide) microspheres," Biomaterials, vol. 18, pp. 893-901 (1997).

Cohen, S., et al., "Controlled Delivery Systems for Proteins Based on Poly(Lactic/Glycolic Acid) Microspheres," Pharmaceutical Research, vol. 8, No. 6, pp. 713-720 (1991).

Collins, J., et al., "Microfluidic flow transducer based on the measurement of electrical admittance", Lab on a Chip, vol. 4, 2004.

Collins, J., et al., "Optimization of Shear Driven Droplet Generation in a Microfluidic Device", ASME International Mechanical Engineering Congress and R&D Expo 2003, Washington.

Cortesi, R., et al., "Production of lipospheres as carriers for bioactive compounds," Biomaterials, vol. 23, pp. 2283-2294 (2002).

Dinsmore, A.D., et al., "Colloidosomes: Selectively Permeable Capsules Composed of Colloidal Particles", Science, Nov. 2002, 298:1006-1009.

Dinsmore, A.D., et al., "Colloidosomes: Selectively-Permeable Capsules Composed of Colloidal Particles", Supplementary Material.

Dove, A., et al., Nature Biotechnology, Dec. 2002, 20:1213.

Edris, A., et al., "Encapsulation of orange oil in a spray dried double emulsion," Nahrung/Food, vol. 45, No. 2, pp. 133-137 (2001).

Eow, J.S., et al. "Electrostatic and hydrodynamic separation of aqueous drops in a flowing viscous oil," Chemical Engineering and Processing, vol. 41, pp. 649-657 (2002).

Eow, J.S., et al., "Electrocoalesce-separators for the separation of aqueous drops from a flowing dielectric viscous liquid," Separation and Purification Technology, vol. 29, pp. 63-77 (2002).

Eow, J.S., et al., "Electrostatic enhancement of coalescence of water droplets in oil: a review of the technology," Chemical Engineering Journal, vol. 85, pp. 357-368 (2002).

Eow, J.S., et al., "Motion, deformation and break-up of aqueous drops in oils under high electric field strengths," Chemical Engineering and Processing, vol. 42, pp. 259-272 (2003).

Eow, J.S., et al., "The bahaviour of a liquid-liquid interface and drop-interface coalescence under the influence of an electric field," Colloids and Surfaces A: Physiochem. Eng. Aspects, pp. 101-123 (2003).

Fisher, J.S., et al., "Cell Encapsulation on a Microfluidic Platform," The Eighth International Conference on Miniaturised Systems for Chemistry and Life Sciences, MicroTAS 2004, Sep. 26-30, Malmo, Sweden.

Fu, A.Y., et al., "A microfabricated fluorescence-activated cell sorter," Nature Biotechnology, vol. 17, pp. 1109-1111 (1999).

Gallarate, M., et al., "On the stability of ascorbic acid in emulsified systems for topical and cosmetic use," International Journal of Pharmaceutics, vol. 188, pp. 233-241 (1999).

Ganan-Calvo, A., "Generation of Steady Liquid Microthreads and MicronSized Monodisperse Sprays in Gas Streams," Physical Review Letters, vol. 80, No. 2 (1998).

Ganan-Calvo, A.M., "Perfectly monodisperse micro-bubble production by novel mechanical means. Scaling laws," American Physical Society 53rd Annual Meeting of the Division of Fluid Dynamics, Nov. 19-21, 2000.

Ganan-Calvo, A.M., "Perfectly Monodisperse Microbubbling by Capillary Flow Focusing," Physical Review Letters, vol. 87, No. 27, pp. 274501-1 to 274501-4 (2001).

Griffiths, A., et al. "Miiaturising the laboratory in emulsion droplets," Trends in Biotechnology 13:1-8, 2006.

Griffiths, A., et al., "Man-made enzymes—from design to in vitro compartmentalisation," Current Opinion in Biotechnology, vol. 11, pp. 338-353 (2000).

Frasland-Mongrain, E. et al., "Droplet coalescence in microfluidic devices" Jan.-Jul. 2003 pp. 1-30.

Hadd, A.G., et al., "Microchip Device for Performing Enzyme Assays," Anal. Chem., vol. 69, pp. 3407-3412 (1997).

Hanes, J., et al., "Degradation of porous poly(anhydride-co-imide) microspheres and implication for controlled macromolecule delivery," Biomaterials, vol. 19, pp. 163-172 (1998).

Hayward, R.C., et al., "Dewetting Instability during the Formation of Polymersomes from Block-Copolymer-Stabilized Double Emulsions," Langmuir, vol. 22, No. 10, pp. 4457-4461 (2006).

Hung, L.H., et al., "Controlled Droplet Fusion in Microfluidic Devices", MicroTAS 2004, Sep. 26-30, Malmo, Sweden.

Hung, L.H., et al., "Optimization of Droplet Generation by controlling PDMS Surface Hydrophobicity," 2004 ASME International Mechanical Engineering Congres and RD&D Expo, Nov. 13-19, 2004, Anaheim, CA.

Jang, J.H., et al., "Controllable delivery of non-viral DNA from porous scaffold," Journal of Controlled Release, vol. 86, pp. 157-168 (2003).

Jo,Y.S., et al, "Encapsulation of Bovine Serum Albumin in Temperature-Programmed "Shell-in-Shell" Structures", Macromol. Rapid Commun., vol. 24, pp. 957-962 (2003).

Kanouni, M., et al., "Preparation of a stable double emulsion (W1/O/W2): role of the interfacial films on the stability of the system", Adv Collid Interf Sci, 99 (2002) 229-254.

Kim, H.K., et al., "Comparative study on sustained release of human growth hormone from semi-crystalline poly(L-lactic acid) and amorphous poly(D,L-lactic-co-glycolic acid) microspheres: morphological effect on protein release," Journal of Controlled Release, vol. 98, pp. 115-125 (2004).

Lamprecht, A., et al., "pH-sensitive microsphere delivery increases oral bioavailability of calcitonin," Journal of Controlled Release, vol. 98, pp. 1-9 (2004).

Leary, J.F., et al., "Application of Advanced Cytometric and Molecular Technologies to Minimal Residual Disease Monitoring," Proceedings of SPIE, vol. 3913, pp. 36-44 (2000).

Lee, D.H., et al., "Effective Formation of Silicone-in-Fluorocarbon-in-Water Double Emulsions: Studies on Droplet Morphology and Stability," Journal of Dispersion Science and Technology, vol. 23, No. 4, pp. 491-497 (2002).

Lee, M.H., et al., "Preparation of Silica Particles Encapsulating Retinol Using O/W/O Multiple Emulsions," Journal of Colloid and Interface Science, vol. 240, pp. 83-89 (2001).

Lemoff, A.V., et al., "An AC Magnetohydrodynamic Microfluidic Switch for Micro Total Analysis Systems", Biomedical Microdevices, 5(1):55-60, 2003.

Link, D.R., et al., "Geometrically Mediated Breakup of Drops in Microfluidic Devices," Physical Review Letters, vol. 92, No. 5 (2004).

Lopez-Herrera, J.M., et al., "Coaxial jets generated from electrified Taylor cones. Scaling laws.," Aerosol Science, vol. 34, pp. 535-552 (2003).

Lopez-Herrera, J.M., et al., "One-Dimensional Simulation of the Breakup of Capillary Jets of Conducting Liquids. Application to E.H.D. Spraying," J. Aerosol. Sci., vol. 30, No. 7, pp. 895-912 (1999).

Lopez-Herrera, J.M., et al., "The electrospraying of viscous and non-viscous semi-insulating liquids. Scalilng laws.," Bulletin of the American Physical Society, vol. 40, No. 12, pp. 2041 (1995).

Lorenceau, E., et al., "Generation of Polymerosomes from Double-Emulsions," Langmuir, vol. 21, pp. 9183-9186 (2005).

Loscertales, I.G., et al., "Micro/Nano Encapsulation via Electrified Coaxial Liquid Jets," Science, vol. 295, pp. 1695-1698 (2002).

Lundstrom, Kenneth, et al., "Breakthrough in cancer therapy: Encapsulation of drugs and viruses", www.currentdrugdiscovery.com, Nov. 2002, 19-23.

Marques, F., et al., "Porous Flow within Concentric Cylinders," Bulletin of the American Physical Society Division of Fluid Dynamics, vol. 41, pp. 1768 (1996).

Nakano, M., et al., "Single-molecule PCR using water-in-oil emulsion," Journal of Biotechnology, vol. 102, pp. 117-124 (2003).

Molecular Probes, ATP Determination Kit (A-22066) (2003).

Nihant, N., et al., "Polylactide Microparticles Prepared by Double Emulsion/Evaporation Technique. I. Effect of Primary Emulsion Stability," Pharmaceutical Research, vol. 11, No. 10, pp. 1479-1484 (1994).

Nisisaki, T., et al. "Controlled Formulation of Monodisperse double emulsions in a multiple-phase microfluidic system" Soft Matter, 2005, 1, 23-27.

Nof, M., et al., "Drug-releasing scaffolds fabricated from drug-loaded microspheres," J. Biomed Mater Res, vol. 59, pp. 349-356, pp. 349-356 (.

Oh, C., et al., "Distribution of Macropores in Silica Particles Prepared by Using Multiple Emulsions," Journal of colloid and Interface Science, vol. 254, pp. 79-86 (2002).

Okushima, S., et al,. "Controlled Production of Monodisperse Double Emulsions by Two-Step Droplet Breakup in Microfluidic Devices," Langmuir, vol. 20, pp. 9905-9908 (2004).

Ouellette, J., "A New Wave of Microfluidic Device," The Industrial Physicist, pp. 14-17, Aug./Sep. 2003.

Piemi, M.P.Y., et al., "Transdermal delivery of glucose through hairless rat skin in vitro: effect of multiple and simple emulsions," International Journal of Pharmecutics, vol. 171, pp. 207-215 (1998).

Raghuraman, B., et al., "Emulsion Liquid Membranes for Wastewater Treatment: Equillibrium Models for Some Typical Metal-Extractant Systems," Environ. Sci. Technol., vol. 28, pp. 1090-1098 (1994).

Schubert, C., et al., "Designer Capsules," Nature Medicine, vol. 8, pp. 1362 (2002).

Silva-Cunha, A., et al., "W/O/W multiple emulsions of insulin containing a protease inhibitor and an absorption enhancer: biological activity after oral administration to normal and diabetic rats," International Journal of Pharmecutics, vol. 169, pp. 33-44 (1998).

Sohn, L.L., et al., "Capacitance cytometry: Measuring biological cells one by one," PNAS, vol. 97, No. 20, pp. 10687-10690 (2000).

Song, H., et al., "A Microfluidic System for Controlling Reaction Networks in Time", Angew Chem. Int Ed, vol. 42(7), pp. 768-772 (2003).

Takeuchi, S., et al., "An Axisymmetric Flow-Focusing Microfluidic Device," Adv. Mater., vol. 17, No. 8, pp. 1067-1072 (2005).

Tan, Y.C., "Microfluidic Liposome Generation from Monodisperse Droplet Emulsion-Towards the Realization of Artificial Cells", Summer Bioengineering Conference, 2003, Florida.

Tan, Y.C., "Monodisperse Droplet Emulsions in Co-Flow Microfluidic Channels", Micro TAS 2003, Lake Tahoe.

Tan, Y.C., et al., "Controlled Fission of Droplet Emulsions in Bifurcating Microfluidic Channels", Transducers 2003, Boston.

Tan, Y.C., et al., "Design of microfluidic channel geometries for the control of droplet volume, chemical concentration, and sorting", Lab Chip, 2004, 4:292-298.

Tawfik, D.S., et al., "Man-made cell-like compartments for molecular evolution," Nature Biotechnology, vol. 16, pp. 652-656 (1998).

Terray, A., et al, "Fabrication of linear colloidal structures for microfluidic applications," Applied Physics Letters, vol. 81, No. 9, pp. 1555-1557 (2002).

Terray, A., et al., "Microfluidic Control Using Colloidal Devices," Science, vol. 296, pp. 1841-1844 (2002).

Thorsen, T., et al., "Dynamic Pattern Formation in a Vesicle-Generating Microfluidic Device," Physical Review Letters, vol. 86, No. 18, pp. 4163-4166 (2001).

Umbanhowar, P.B., et al., "Monodisperse Emulsion Generation via Drop Break Off in a Coflowing Stream," Langmuir, vol. 16, pp. 347-351 (2000).

Utada, A.S., et al., "Monodisperse Double Emulsions Generated from a Microcapillary Device", Science, vol. 308, pp. 537-541 (2005).

Wolff, A., et al., "Integrating advanced functionality in a microfabricated high-throughput fluorescent-activated cell sorter," Lab Chip, vol. 3, pp. 22-27 (2003).

Xu, S., et al., "Generation of Monodisperse Particles by Using Microfluidics: Control over Size, Shape and Composition," Angew. Chem. Int. Ed., vol. 43, pp. 2-5 (2004).

Yamaguchi, Y., et al., "Insulin-loaded biodegradable PLGA microcapsules: initial burst release controlled by hydrophilic additives," Journal of Controlled Release, vol. 81, pp. 235-249 (2002).

Zhang, J.H., et al., "A Simple Statistical Parameter for Use in Evaluation and Validation of High Throughput Screening Assays," Journal of Biomolecular Screening, vol. 4, No. 2, pp. 67-73 (1999).

Zheng, B., et al., "A Microfluidic Approach for Screening Submicroliter Volumes against Multiple Reagents by Using Performed Arrays of Nanoliter Plugs in a Three-Phase Liquid/Liquid/Gas Flow," Angew. Chem. Int. Ed., vol. 44, pp. 2520-2523 (2005).

International Search Report dated Dec. 20, 2004 in PCT/US2004/010903.

Written Opinion dated Dec. 17, 2004 in PCT/US2004/010903.

International Preliminary Report Oct. 14, 2005 in PCT/US2004/010903.

International Search Report dated Feb. 6, 2004 in PCT/US2003/20542.

International Preliminary Report dated Feb. 27, 2006 in PCT/US2004/027912.

Written Opinion dated Jan. 26, 2005 in PCT/US2004/027912.

International Search Report dated May 31, 2006 in PCT/US2006/001938.

Written Opinion dated May 31, 2006 in PCT/US2006/001938.

International Search Report dated Jun. 16, 2006 in PCT/US2006/007772.

Written Opinion dated Jun. 16, 2006 in PCT/US2006/007772.

International Search Report dated Oct. 9, 2007 in PCT/US2007/002063.

Office Action dated Nov. 8, 2007 for U.S. Appl. No. 11/246,911.

Office Action dated Jun. 3, 2008 for U.S. Appl. No. 11/246,911.

Office Action dated Dec. 18, 2008 for U.S. Appl. No. 11/246,911.

Office Action dated Dec. 14, 2007 in U.S. Appl. No. 11/024,228.

Office Action dated Jul. 9, 2008 for U.S. Appl. No. 11/024,228.

Office Action dated Dec. 11, 2008 for U.S. Appl. No. 11/024,228.

Office Action dated Dec. 19, 2008 for U.S. Appl. No. 11/368,263.

International Search Reported dated Mar. 4, 2009 in PCT/US2008/004097.

Nisisako, "Microstructured Devices for Preparing Controlled Multiple Emulsions," Chem. Eng. Technol., vol. 8, No. 31, pp. 1091-1098 (2008).

Okushima, et al., "Controlled production of monodisperse double emulsions by two-step droplet breakup in microfluidic devices," Langmuir, vol. 20, No. 23, pp. 9905-9908 (2004).

Pannacci, N., et al., "Equilibrium and Nonequilibrium States in Microfluidic Double Emulsions," The American Physical Society, vol. 101, pp. 164502-1-164502-4 (2008).

Priest, "Generation of monodisperse gel emulsions in a microfluidic device", Apl Phys Lett. 88:024106 (2006).

Seo, M., et al., "Microfluidic consecutive flow-focusing droplet generators," Soft Matter, vol. 3, pp. 986-992 (2007).

Zimmerman, et al, "Microscale production of hybridomas by hypo-osmolar electrofusion," Hum. Antibod. Hybridomas, vol. 3, pp. 14-18 (1992).

Experimental Soft Condensed Matter Group, "Cool Picture of the Moment," http://www.seas.harvard.edu/projects /weitzlab/coolpic16012007.html dated Jan. 16, 2007.

International Search Report and Written Opinion from PCT Application PCT/US2008/004097, dated Aug. 10, 2009.

Chang et al. "Controlled double emulsification utilizing 3D PDMS microchannels" Journal of Micromechanics and Microengineering 18 (2008) pp. 1-8.

Chu et al. "Controllable Monodisperse Multiple Emulsions" Angew. Chem. Ed. 2007, 46, 8970-8974.

* cited by examiner

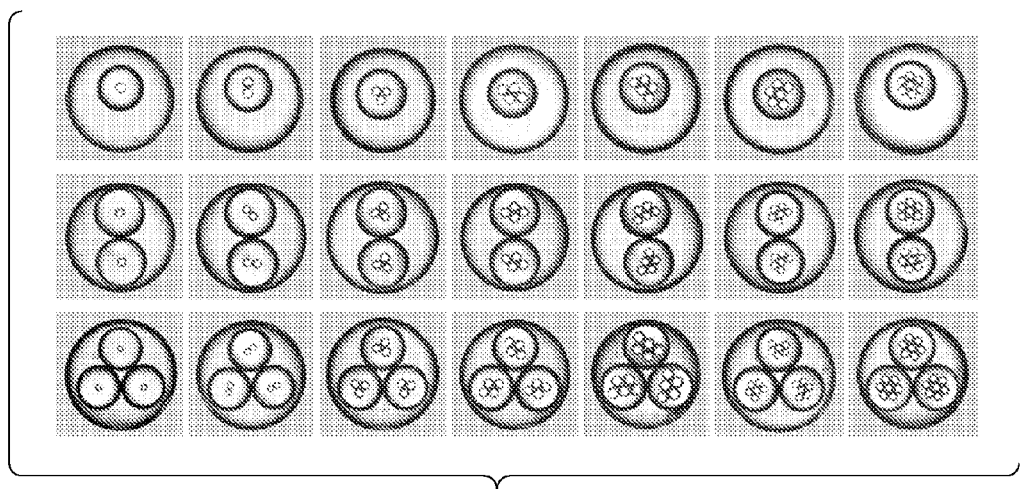
Fig. 5E
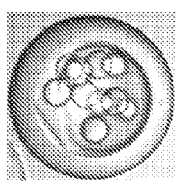 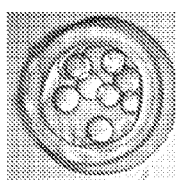 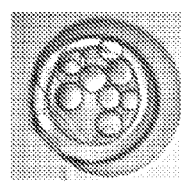 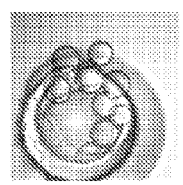 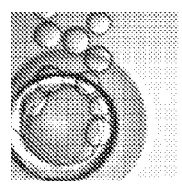
Fig. 5F    Fig. 5G    Fig. 5H    Fig. 5I    Fig. 5J

EMULSIONS AND TECHNIQUES FOR FORMATION

RELATED APPLICATIONS

This application claims the benefit of U.S. Provisional Patent Application Ser. No. 60/920,574, filed Mar. 28, 2007, entitled "Multiple Emulsions and Techniques for Formation," by Chu, et al., incorporated herein by reference.

GOVERNMENT FUNDING

This invention was made with U.S. government support under DMR-0213805 and DMR-0602684 awarded by the National Science Foundation. The U.S. Government has certain rights in the invention.

FIELD OF INVENTION

The present invention relates generally to emulsions and the production of emulsions, including multiple emulsions and microfluidic systems for producing multiple emulsions, and techniques for using the same.

BACKGROUND

An emulsion is a fluidic state which exists when a first fluid is dispersed in a second fluid that is typically immiscible or substantially immiscible with the first fluid. Examples of common emulsions are oil in water and water in oil emulsions. Multiple emulsions are emulsions that are formed with more than two fluids, or two or more fluids arranged in a more complex manner than a typical two-fluid emulsion. For example, a multiple emulsion may be oil-in-water-in-oil ("o/w/o"), or water-in-oil-in-water ("w/o/w"). Multiple emulsions are of particular interest because of current and potential applications in fields such as pharmaceutical delivery, paints and coatings, food and beverage, chemical separations, and health and beauty aids.

Typically, multiple emulsions of a droplet inside another droplet are made using a two-stage emulsification technique, such as by applying shear forces through mixing to reduce the size of droplets formed during the emulsification process. Other methods such as membrane emulsification techniques using, for example, a porous glass membrane, have also been used to produce water-in-oil-in-water emulsions. Microfluidic techniques have also been used to produce droplets inside of droplets using a procedure including two or more steps. For example, see International Patent Application No. PCT/US2004/010903, filed Apr. 9, 2004, entitled "Formation and Control of Fluidic Species," by Link, et al., published as WO 2004/091763 on Oct. 28, 2004; or International Patent Application No. PCT/US03/20542, filed Jun. 30, 2003, entitled "Method and Apparatus for Fluid Dispersion," by Stone, et al., published as WO 2004/002627 on Jan. 8, 2004, each of which is incorporated herein by reference. See also Anna, et al., "Formation of Dispersions using 'Flow Focusing' in Microchannels," *Appl. Phys. Lett.*, 82:364 (2003) and Okushima, et al., "Controlled Production of Monodispersed Emulsions by Two-Step proplet Breakup in Microfluidic Devices," *Langmuir* 20:9905-9908 (2004). In some of these examples, a T-shaped junction in a microfluidic device is used to first form an aqueous droplet in an oil phase, which is then carried downstream to another T-junction where the aqueous droplet contained in the oil phase is introduced into another aqueous phase. In another technique, co-axial jets can be used to produce coated droplets, but these coated droplets must be re-emulsified into the continuous phase in order to form a multiple emulsion. See Loscertales et al., "Micro/Nano Encapsulation via Electrified Coaxial Liquid Jets," *Science* 295:1695 (2002).

Multiple emulsions and the products that can be made from them can be used to produce a variety of products useful in the food, coatings, cosmetic, chemical, or pharmaceutical industries, for example. Methods for producing multiple emulsions providing consistent droplet sizes, consistent droplet counts, consistent coating thicknesses, and/or improved control would make commercial implementation of these products more viable.

SUMMARY OF THE INVENTION

The present invention relates generally to emulsions and the production of emulsions, including multiple emulsions and microfluidic systems for producing multiple emulsions, and techniques for using the same. The subject matter of the present invention involves, in some cases, interrelated products, alternative solutions to a particular problem, and/or a plurality of different uses of one or more systems and/or articles.

In one aspect, the invention is directed to an article. In a first set of embodiments, the article includes a plurality of outer fluidic droplets, where substantially all of the outer fluidic droplets each contain two or more first fluidic droplets each containing one or more second fluidic droplets. In some cases, each of the plurality of first fluidic droplets contains substantially the same number of second fluidic droplets therein. The article, in another set of embodiments, includes a plurality of outer fluidic droplets. In some cases, substantially all of the outer fluidic droplets contain one or more first fluidic droplets each containing two or more second fluidic droplets.

In yet another set of embodiments, the article includes a plurality of outer fluidic droplets, where substantially all of the outer fluidic droplets contain one or more first fluidic droplets. In one embodiment, each of the one or more first fluidic droplets contain one or more second fluidic droplets, such that the outer fluidic droplets each contain more than one of the first fluidic droplets and/or more than one second fluidic droplets.

The article, according to still another embodiment, includes a plurality of fluidic droplets. In some cases, substantially all of the fluidic droplets contain more than one nesting level of fluidic droplets therein, where a nesting level is defined by one or more fluidic droplets each contained within a surrounding fluidic droplet. In one embodiment, in at least one nesting level, there is a nesting level defined by more than one fluidic droplet each contained within a surrounding fluidic droplet.

In another aspect, the invention is directed to an apparatus for forming droplets. The apparatus includes a first conduit, a second conduit including an end defining an exit opening that opens into the first conduit, and a third conduit including an end defining an exit opening that opens into the second conduit, according to one set of embodiments. In some instances, the exit opening of the third conduit is not contained within the first conduit. In one embodiment, the first conduit is constructed and arranged to allow a fluid to flow around at least a portion of the second conduit contained within the first conduit, and the second conduit is constructed and arranged to allow a fluid to flow around at least a portion of the third conduit contained within the second conduit.

In one set of embodiments, the apparatus comprises a first conduit comprising a first portion and a second portion, a second conduit comprising an end defining an exit opening, and a third conduit comprising an end defining an entrance opening. In some cases, at least a portion of the second conduit is disposed in the first and third conduits, and the second conduit passes through the first portion of the first conduit and the exit opening of the third conduit but not through the second portion of the first conduit. In one embodiment, at least a portion of the third conduit is disposed in the first conduit, and the third conduit passes through the second portion of the first conduit but not the first portion of the first conduit. In certain cases, at least one of the first, second, or third conduits has an average diameter of less than 1 mm.

In another set of embodiments, the apparatus comprises a first conduit having a first portion and a second portion, a second conduit passing through the first portion of the first conduit but not the second portion, and a third conduit passing the second portion of the first conduit but not the first portion. In some cases, the second conduit includes an end defining an exit opening that opens into the third conduit, and in certain embodiments, at least one of the first, second, or third conduits has an average diameter of less than 1 mm.

The invention, in yet another aspect, is a method of packaging a species. In one set of embodiments, the method includes acts of suspending a species in a first fluid, flowing the first fluid in a stream surrounded by a second fluid stream, where the second fluid is substantially immiscible with the first fluid, introducing a third fluid stream that surrounds the second fluid stream, and forming multiple droplets of the first fluid, each contained within a second fluidic droplet, where the droplets contain at least one of the species. According to another set of embodiments, the method includes acts of providing a plurality of outer fluidic droplets each containing a plurality of inner fluidic droplets, and causing at least some of the outer fluidic droplets to release the inner fluidic droplets.

In one aspect, the invention is directed to a method for forming droplets. The method includes, according to one set of embodiments, flowing a first fluid in a first conduit; flowing a second fluid in a second conduit and expelling the second fluid, from an end defining an exit opening of the second conduit, into the first fluid in the first conduit; urging the second fluid, surrounded by the first fluid, into a first restriction under conditions in which droplets of the second fluid in the first fluid are formed within the restriction; releasing the droplets of the second fluid carried in the first fluid from the first restriction into a region having a dimension larger than the first restriction, thereby forming an emulsion; flowing a third fluid in a third conduit; expelling the emulsion, from an end defining an exit opening of the first conduit, into the third fluid in the third conduit; urging the emulsion, surrounded by the third fluid, into a second restriction under conditions in which the emulsion forms droplets within the third fluid within the second restriction; and releasing the droplets of emulsion carried in the third fluid from the second restriction into a region having a dimension larger than the second restriction, thereby forming a multiple emulsion.

In another aspect, the present invention is directed to a method of making one or more of the embodiments described herein, for example, a multiple emulsion. In another aspect, the present invention is directed to a method of using one or more of the embodiments described herein, for example, a multiple emulsion.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 5A-5J illustrate yet another microfluidic device useful in making multiple emulsions, according to another embodiment of the invention, and droplets formed from such a device;

DETAILED DESCRIPTION

Figure 1:
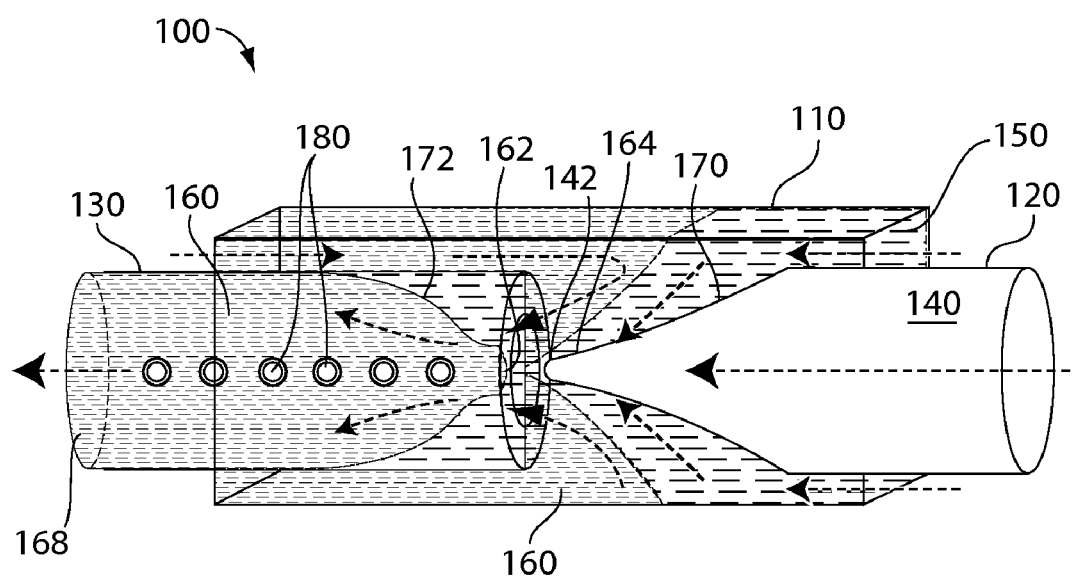
FIG. 1 is a schematic illustration of a microfluidic device useful in making multiple emulsions, according to one embodiment of the invention.

The present invention generally relates to emulsions such as multiple emulsions, and to methods and apparatuses for making emulsions, and techniques for using the same. A multiple emulsion generally describes larger droplets that contain one or more smaller droplets therein which, in some cases, can contain even smaller droplets therein, etc. Emulsions, including multiple emulsions, can be formed in certain embodiments with generally precise repeatability, and can be tailored to include any number of inner droplets, in any desired nesting arrangement, within a single outer droplet. In addition, in some aspects of the invention, one or more droplets may be controllably released from a surrounding droplet.

Fields in which emulsions, including multiple emulsions, may prove useful include, for example, food, beverage, health and beauty aids, paints and coatings, chemical separations, and drugs and drug delivery. For instance, a precise quantity of a drug, pharmaceutical, or other agent can be encapsulated by a shell designed to release its contents under particular conditions, as described in detail below. In some instances, cells can be contained within a droplet, and the cells can be stored and/or delivered. Other species that can be stored and/or delivered include, for example, biochemical species such as nucleic acids such as siRNA, RNAi and DNA, proteins, peptides, or enzymes. Additional species that can be incorporated within an emulsion of the invention include, but are not limited to, nanoparticles, quantum dots, fragrances, proteins, indicators, dyes, fluorescent species, chemicals, or the like. An emulsion can also serve as a reaction vessel in certain cases, such as for controlling chemical reactions, or for in vitro transcription and translation, e.g., for directed evolution technology.

Using the methods and devices described herein, in some embodiments, a consistent size and/or number of droplets can be produced, and/or a consistent ratio of size and/or number of outer droplets to inner droplets, inner droplets to other inner droplets, or other such ratios, can be produced. For example, in some cases, a droplet of predictable size can be used to provide a specific quantity of a drug. In addition, combinations of compounds or drugs may be stored, transported, or delivered in an emulsion droplet. For instance, hydrophobic and hydrophilic species can be delivered in a single, multiple emulsion droplet, as the droplet can include both hydrophilic and hydrophobic portions. The amount and concentration of each of these portions can be consistently controlled according to certain embodiments of the invention, which can provide for a predictable and consistent ratio of two or more species in the multiple emulsion droplet.

Various aspects of the present invention are generally directed to multiple emulsions, which includes larger fluidic droplets that contain one or more smaller droplets therein which, in some cases, can contain even smaller droplets therein, etc. In some cases, the multiple emulsion is surrounded by a liquid (e.g., suspended). Any of these droplets may be of substantially the same shape and/or size (i.e., "monodisperse"), or of different shapes and/or sizes, depending on the particular application. As used herein, the term "fluid" generally refers to a substance that tends to flow and to conform to the outline of its container, i.e., a liquid, a gas, a viscoelastic fluid, etc. Typically, fluids are materials that are unable to withstand a static shear stress, and when a shear stress is applied, the fluid experiences a continuing and permanent distortion. The fluid may have any suitable viscosity that permits flow. If two or more fluids are present, each fluid may be independently selected among essentially any fluids (liquids, gases, and the like) by those of ordinary skill in the art, by considering the relationship between the fluids. In some cases, the droplets may be contained within a carrier fluid, e.g., a liquid. It should be noted, however, that the present invention is not limited to only multiple emulsions. In some embodiments, single emulsions can also be produced.

A "droplet," as used herein, is an isolated portion of a first fluid that is surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located.

In certain instances, the droplets may be contained within a carrying fluid, e.g., within a fluidic stream. The fluidic stream, in one set of embodiments, is created using a microfluidic system, discussed in detail below. In some cases, the droplets will have a homogenous distribution of diameters, i.e., the droplets may have a distribution of diameters such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter of the droplets. Techniques for producing such a homogenous distribution of diameters are also disclosed in International Patent Application No. PCT/US2004/010903, filed Apr. 9, 2004, entitled "Formation and Control of Fluidic Species," by Link, et al., published as WO 2004/091763 on Oct. 28, 2004, incorporated herein by reference, and in other references as described below.

The fluidic droplets (in any nesting level, in the case of a multiple emulsion) may each be substantially the same shape and/or size. Typically, monodisperse droplets are of substantially the same size. The shape and/or size of the fluidic droplets can be determined, for example, by measuring the average diameter or other characteristic dimension of the droplets. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The average diameter of a single droplet, in a non-spherical droplet, is the diameter of a perfect sphere having the same volume as the non-spherical droplet. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements.

One aspect of the present invention is generally directed to multiple emulsions, which includes larger fluidic droplets that contain one or more smaller droplets therein which, in some cases, can contain even smaller droplets therein, etc. Any number of nested fluids can be produced as discussed in detail below, and accordingly, additional third, fourth, fifth, sixth, etc. fluids may be added in some embodiments of the invention to produce increasingly complex droplets within droplets. For example, an outer fluidic droplet may contain one, two, three, four, or more first fluidic droplets (i.e., composed of a first fluid), some or all of which can contain one, two, three, four, or more second fluidic droplets (i.e., composed of a second fluid).

Some of these fluids may be the same, in certain embodiments of the invention (e.g., the second fluid may have the same composition as the outer fluid). There may be any number of nestings present. For example, the second fluidic droplets may contain one, two, three, four, or more third fluidic droplets; optionally, the third fluidic droplets may contain one, two, three, four, or more fourth fluidic droplets, and so on. Within each nesting level (defined by one or more fluidic droplets each contained within a surrounding fluidic droplet), any number of fluidic droplets may be present, for example, for any given nesting level, one, two, three, four, or more fluidic droplets may be contained within a surrounding fluidic droplet. In addition, the number of the droplets in each nesting level may be controlled independently of the number of droplets in other nesting levels. In certain cases, any of these droplets may contain one or more species (e.g., molecules, cells, particles, etc.), as described below. For example, the species may be contained within the innermost droplet(s) of a nesting of droplets.

In some cases, for a given nesting level, each of the fluidic droplets of that level may contain substantially the same number of inner fluidic droplets therein; for example, substantially all of the outer fluidic droplets may contain substantially the same number of first fluidic droplets, and/or substantially all of the first fluidic droplets may contain substantially the same number of second fluidic droplets therein, etc. It should be understood that, even if the droplets appear to be substantially identical, or to contain substantially the same number of droplets therein, not all of the droplets will necessarily be completely identical. In some cases, there may be minor variations in the number and/or size of droplets contained within a surrounding droplet. Thus, in some cases, at least about 75%, at least about 80%, at least about 85%, at least about 90%, at least about 92%, at least about 94%, at least about 95%, at least about 96%, at least about 97%, at least about 98%, or at least about 99% of a plurality of outer droplets may each contain the same number of first fluidic droplets therein, and/or the same number of second fluidic droplets therein, etc. Similarly, in some embodiments, at least about 75%, at least about 80%, at least about 85%, at least about 90%, at least about 92%, at least about 94%, at least about 95%, at least about 96%, at least about 97%, at least about 98%, or at least about 99% of a plurality of first droplets may each contain the same number of second droplets therein, etc.

In some embodiments, however, a plurality of outer droplets each may not necessarily contain substantially the same number of inner fluidic droplets therein, but each of the plurality of outer droplets contains two or more first fluidic droplets, some or all of which can contain second fluidic droplets (and optionally, third fluidic droplets nested within the second fluidic droplets, etc. For example, at least about 75%, at least about 80%, at least about 85%, at least about 90%, at least about 92%, at least about 94%, at least about 95%, at least about 96%, at least about 97%, at least about 98%, or at least about 99% of a plurality of outer fluidic droplets may each contain more than two first fluidic droplets, and/or one or more second fluidic droplets, etc.

As a non-limiting example, in one set of embodiments, a triple emulsion may be produced, i.e., an emulsion containing a carrying fluid, containing droplets containing an outer fluid, some of which droplets can contain one or more inner fluidic droplets therein. Micrographs of various triple emulsions, containing varying number of fluidic droplets therein, are shown in FIG. 3. In some cases, the carrying fluid and the inner fluid may be the same. The fluids in the triple emulsion are often of varying miscibilities, due to differences in hydrophobicity. For example, the carrying fluid may be water soluble (i.e., miscible in water), the outer fluid oil soluble (or immiscible in water), and the inner fluid water soluble. This arrangement is often referred to as a w/o/w multiple emulsion ("water/oil/water"). Another multiple emulsion may include a carrying fluid that is oil soluble (or immiscible in water), an outer fluid that is water soluble, and an inner fluid that is oil soluble. This type of multiple emulsion is often referred to as an o/w/o multiple emulsion ("oil/water/oil"). It should be noted that the term "oil" in the above terminology merely refers to a fluid that is generally more hydrophobic and not miscible in water, as is known in the art. Thus, the oil may be a hydrocarbon in some embodiments, but in other embodiments, the oil may comprise other hydrophobic fluids.

More specifically, as used herein, two fluids are immiscible, or not miscible, with each other when one is not soluble in the other to a level of at least 10% by weight at the temperature and under the conditions at which the emulsion is produced. For instance, two fluids may be selected to be immiscible within the time frame of the formation of the fluidic droplets. In some embodiments, the carrying and inner fluids are compatible, or miscible, while the outer fluid is incompatible or immiscible with one or both of the carrying and inner fluids. In other embodiments, however, all three fluids may be mutually immiscible, and in certain cases, all of the fluids do not all necessarily have to be water soluble. In still other embodiments, as mentioned, additional fourth, fifth, sixth, etc. fluids may be added to produce increasingly complex droplets within droplets, e.g., an outer fluid may surround a first fluid, which may in turn surround a second fluid, which may in turn surround a third fluid, which in turn surround a fourth fluid, etc. In addition, the physical properties of each nesting layer of fluidic droplets may each be independently controlled, e.g., by control over the composition of each nesting level.

The fluids within the multiple emulsion droplet may the same, or different. The fluids may be chosen such that the inner droplets remain discrete, relative to their surroundings. As non-limiting examples, a fluidic droplet may be created having an outer droplet, containing one or more first fluidic droplets, some or all of which may contain one or more second fluidic droplets. In some cases, the outer fluid and the second fluid may be identical or substantially identical; however, in other cases, the outer fluid, the first fluid, and the second fluid may be chosen to be essentially mutually immiscible. One non-limiting example of a system involving three essentially mutually immiscible fluids is a silicone oil, a mineral oil, and an aqueous solution (i.e., water, or water containing one or more other species that are dissolved and/or suspended therein, for example, a salt solution, a saline solution, a suspension of water containing particles or cells, or the like). Another example of a system is a silicone oil, a fluorocarbon oil, and an aqueous solution. Yet another example of a system is a hydrocarbon oil (e.g., hexadecane), a fluorocarbon oil, and an aqueous solution. Non-limiting examples of suitable fluorocarbon oils include octadecafluorodecahydronaphthalene:

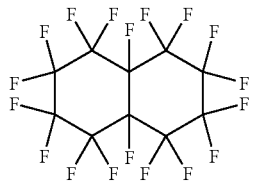

or 1-(1,2,2,3,3,4,4,5,5,6,6-undecafluorocyclohexyl)ethanol:

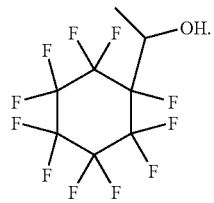

In the descriptions herein, multiple emulsions are often described with reference to a three phase system, i.e., having a carrying fluid, an outer fluid, and an inner fluid. However, it should be noted that this is by way of example only, and that in other systems, additional fluids may be present within the multiple emulsion droplet. Accordingly, it should be understood that the descriptions of the carrying fluid, outer fluid, and inner fluid are by way of ease of presentation, and that the descriptions herein are readily extendable to systems involving additional fluids, e.g., quadruple emulsions, quintuple emulsions, sextuple emulsions, septuple emulsions, etc.

As fluid viscosity can affect droplet formation, in some cases the viscosity of any of the fluids in the fluidic droplets may be adjusted by adding or removing components, such as diluents, that can aid in adjusting viscosity. For example, in some embodiments, the viscosity of the outer fluid and the first fluid are equal or substantially equal. This may aid in, for example, an equivalent frequency or rate of droplet formation in the outer and fluid fluids. In other embodiments, the viscosity of the first fluid may be equal or substantially equal to the viscosity of the second fluid, and/or the viscosity of the outer fluid may be equal or substantially equal to the viscosity of the second fluid. In yet another embodiment, the outer fluid may exhibit a viscosity that is substantially different from either the first or second fluids. A substantial difference in viscosity means that the difference in viscosity between the two fluids can be measured on a statistically significant basis. Other distributions of fluid viscosities within the droplets are also possible. For example, the second fluid may have a viscosity greater than or less than the viscosity of the first fluid (i.e., the viscosities of the two fluids may be substantially different), the first fluid may have a viscosity that is greater than or less than the viscosity of the outer fluid, etc. It should also be noted that, in higher-order droplets, e.g., containing four, five, six, or more fluids, the viscosities may also be independently selected as desired, depending on the particular application.

In one set of embodiments, one or more fluids within an emulsion may be polymerized, e.g., to form a polymerosome, e.g., comprising a bilayer of polymers and/or other species. For instance, in some cases, one or more of the fluids forming the emulsion may include polymers, such as copolymers, which can be subsequently polymerized. An example of such a system is normal butyl acrylate and acrylic acid, which can be polymerized to form a copolymer of poly(normal-butyl acrylate)-poly(acrylic acid).

In certain embodiments of the invention, the fluidic droplets may contain additional entities or species, for example, other chemical, biochemical, or biological entities (e.g., dissolved or suspended in the fluid), cells, particles, gases, molecules, pharmaceutical agents, drugs, DNA, RNA, proteins, fragrance, reactive agents, biocides, fungicides, preservatives, chemicals, or the like. Cells, for example, can be suspended in a fluid emulsion, or contained in a polymerosome. Thus, the species may be any substance that can be contained in any portion of a droplet and can be differentiated from the droplet fluid. The species may be present in any fluidic droplet, for example, within an inner droplet and/or within an outer droplet, etc. In some cases, the droplets may each be substantially the same shape or size, as discussed above.

As the polydispersity and size of the droplets can be narrowly controlled, emulsions can be formed that include a specific number of species or particles per droplet. For instance, a single droplet may contain 1, 2, 3, 4, or more species. The emulsions can be formed with low polydispersity so that greater than 90%, 95%, or 99% of the droplets formed contain the same number of species. In certain instances, the invention provides for the production of droplets consisting essentially of a substantially uniform number of entities of a species therein (i.e., molecules, cells, particles, etc.). For example, at least about 75%, at least about 80%, at least about 85%, at least about 90%, at least about 92%, at least about 94%, at least about 95%, at least about 96%, at least about 97%, at least about 98%, or at least about 99%, or more of a plurality or series of droplets may each contain at least one entity, and/or may contain the same number of entities of a particular species. For instance, a substantial number of fluidic droplets produced, e.g., as described above, may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may each independently contain a range of entities, for example, less than 20 entities, less than 15 entities, less than 10 entities, less than 7 entities, less than 5 entities, or less than 3 entities in some cases.

In one set of embodiments, in a plurality of droplets of fluid, some of which contain a species of interest and some of which do not contain the species of interest, the droplets of fluid may be screened or sorted for those droplets of fluid containing the species, and in some cases, the droplets may be screened or sorted for those droplets of fluid containing a particular number or range of entities of the species of interest. Systems and methods for screening and/or sorting droplets are disclosed in, for example, U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007, incorporated herein by reference.

Thus, in some cases, a plurality or series of fluidic droplets, some of which contain the species and some of which do not, may be enriched (or depleted) in the ratio of droplets that do contain the species, for example, by a factor of at least about 2, at least about 3, at least about 5, at least about 10, at least about 15, at least about 20, at least about 50, at least about 100, at least about 125, at least about 150, at least about 200, at least about 250, at least about 500, at least about 750, at least about 1000, at least about 2000, or at least about 5000 or more in some cases. In other cases, the enrichment (or depletion) may be in a ratio of at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, or more. For example, a fluidic droplet containing a particular species may be selected from a library of fluidic droplets containing various species, where the library may have about $10^5$, about $10^6$, about $10^7$, about $10^8$, about $10^9$, about $10^{10}$, about $10^{11}$, about $10^{12}$, about $10^{13}$, about $10^{14}$, about $10^{15}$, or more items, for example, a DNA library, an RNA library, a protein library, a combinatorial chemistry library, etc. In certain embodiments, the droplets carrying the species may then be fused, reacted, or otherwise used or processed, etc., as further described herein, for example, to initiate or determine a reaction.

In one set of embodiments, the fluidic droplets may contain cells or other entities, such as proteins, viruses, macromolecules, particles, etc. As used herein, a "cell" is given its ordinary meaning as used in biology. One or more cells and/or one or more cell types can be contained in a droplet. The inner fluid may be, for example, an aqueous buffer solution. The cell may be any cell or cell type. For example, the cell may be a bacterium or other single-cell organism, a plant cell, or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. In certain embodiments, the cell may be a Chinese hamster ovarian ("CHO") cell or a 3T3 cell.

For example, an emulsion can be formed in which greater than about 95% of the droplets formed contain a single cell at the point of droplet production, without a need to separate or otherwise purify the emulsion in order to obtain this level of dispersity. Typically, the fluid supporting the cell is the innermost fluid and is aqueous based. The surrounding fluid may be a non-aqueous fluid and other fluids, e.g., within an emulsion, may be aqueous or non-aqueous. If a polymerosome is used, the shell surrounding the cell (which may or may not be the outermost fluidic droplet in a multiple emulsion) may be formed of a material capable of protecting the cell. The shell may help retain, for example, moisture, and can be sized appropriately to maximize the lifetime of the cell within the polymerosome. For instance, the shell may be sized to contain a specific volume, e.g., 10 nL, of inner fluid as well as a single cell or a select number of cells. Likewise, cells may be suspended so that, statistically, one cell will be included with each aliquot (e.g., 10 nL) of fluid within a droplet.

In one aspect of the present invention, multiple emulsions are formed by flowing three (or more) fluids through a system of conduits. The system may be a microfluidic system. "Microfluidic," as used herein, refers to a device, apparatus or system including at least one fluid channel having a cross-sectional dimension of less than about 1 millimeter (mm), and in some cases, a ratio of length to largest cross-sectional dimension of at least 3:1. One or more conduits of the system may be a capillary tube. In some cases, multiple conduits are provided, and in some embodiments, at least some are nested, as described herein. The conduits may be in the microfluidic size range and may have, for example, average inner diameters, or portions having an inner diameter, of less than about 1 millimeter, less than about 300 micrometers, less than about 100 micrometers, less than about 30 micrometers, less than about 10 micrometers, less than about 3 micrometers, or less than about 1 micrometer, thereby providing droplets having comparable average diameters. One or more of the conduits may (but not necessarily), in cross section, have a height that is substantially the same as a width at the same point. Conduits may include an orifice that may be smaller, larger, or the same size as the average diameter of the conduit. For example, conduit orifices may have diameters of less than about 1 mm, less than about 500 micrometers, less than about 300 micrometers, less than about 200 micrometers, less than about 100 micrometers, less than about 50 micrometers, less than about 30 micrometers, less than about 20 micrometers, less than about 10 micrometers, less than about 3 micrometers, etc. In cross-section, the conduits may be rectangular or substantially non-rectangular, such as circular or elliptical. The conduits of the present invention can also be disposed in or nested in another conduit, and multiple nestings are possible in some cases. In some embodiments, one conduit can be concentrically retained in another conduit and the two conduits are considered to be concentric. However, one concentric conduit may be positioned off-center with respect to another, surrounding conduit, i.e., "concentric" does not necessarily refer to tubes that are strictly coaxial. By using a concentric or nesting geometry, the inner and outer fluids, which are typically miscible, may avoid contact, which can facilitate great flexibility in making emulsions such as multiple emulsions and in devising techniques for encapsulation and polymerosome formation. For example, this technique allows for fabrication of core-shell structure, and these core-shell structures can be converted into capsules.

A "channel," as used herein, means a feature on or in an article (substrate) that at least partially directs flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 mm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

As the systems described herein may be three-dimensional microfluidic devices, e.g., having concentric conduit arrangements, a fluid (of any nesting level of a multiple emulsion) can be completely shielded from a surrounding fluid in certain embodiments. This may reduce or eliminate problems that can occur in other systems, when the fluids may contact each other at or near a solid surface, such as in a two-dimensional system.

In some embodiments, a flow pathway can exist in an inner conduit and a second flow pathway can be formed in a coaxial space between the external wall of the interior conduit and the internal wall of the exterior conduit, as discussed in detail below. The two conduits may be of different cross-sectional shapes in some cases. In one embodiment, a portion or portions of an interior conduit may be in contact with a portion or portions of an exterior conduit, while still maintaining a flow pathway in the coaxial space. Different conduits used within the same device may be made of similar or different materials. For example, all of the conduits within a specific device may be glass capillaries, or all of the conduits within a device may be formed of a polymer, for example, polydimethylsiloxane, as discussed below.

A geometry that provides coaxial flow can also provide hydrodynamic focusing of that flow, according to certain embodiments of the invention. Many parameters of the droplets, including any suitable nesting layer in a multiple emulsion droplet, can be controlled using hydrodynamic focusing. For instance, droplet diameter, outer droplet thickness and the total number of inner droplets per droplet can be controlled.

The emulsion parameters can also be engineered by adjusting, for example, the system geometry, and/or the flowrate of any of the fluids used to form the emulsion droplets. For example as shown in FIG. 5E, by controlling the flowrates of the fluids, different numbers of droplets can be nested within a multiple emulsion droplet. By controlling these flow rates independently, the number of droplets and/or the thickness or other dimensions of any of the droplets can be predicatively chosen.

The schematic diagram illustrated in FIG. 1 shows one embodiment of the invention including a device 100 having an outer conduit 110, a first inner conduit (or injection tube) 120, and a second inner conduit (or collection tube) 130. An inner fluid 140 is shown flowing in a right to left direction and middle fluid 150 flows in a right to left direction in the space outside of injection tube 120 and within conduit 110. Outer fluid 160 flows in a left to right direction in the pathway provided between outer conduit 110 and collection tube 130. After outer fluid 160 contacts middle fluid 150, it changes direction and starts to flow in substantially the same direction as the inner fluid 140 and the middle fluid 150, right to left. Injection tube 120 includes an exit orifice 164 at the end of tapered portion 170. Collection tube 130 includes an entrance orifice 162, an internally tapered surface 172, and exit channel 168. Thus, the inner diameter of injection tube 120 decreases in a direction from right to left, as shown, and the inner diameter of collection tube 130 increases from the entrance orifice in a direction from right to left. These constrictions, or tapers, can provide geometries that aid in producing consistent emulsions. The rate of constriction may be linear or non-linear.

As illustrated in FIG. 1, inner fluid 140 exiting from orifice 164 can be completely surrounded by middle fluid 150, as there is no portion of inner fluid 140 that contacts the inner surface of conduit 110 after its exit from injection tube 120. Thus, for a portion between exit orifice 164 to a point inside of collection tube 130 (to the left of entrance orifice 162), a stream of fluid 140 is concentrically surrounded by a stream of fluid 150. Additionally, middle fluid 150 may not come into contact with the surface of collection tube 130, at least until after the multiple emulsion has been formed, because it is concentrically surrounded by outer fluid 160 as it enters collection tube 130. Thus, from a point to the left of exit orifice 164 to a point inside of collection tube 130, a composite stream of three fluid streams is formed, including inner fluid 140 concentrically surrounded by a stream of middle fluid 150, which in turn is concentrically surrounded by a stream of outer fluid 160. The inner and middle fluids do not typically break into droplets until they are inside of collection tube 130 (to the left of entrance orifice 162). Under "dripping" conditions, the droplets are formed closer to the orifice, while under "jetting" conditions, the droplets are formed further downstream, i.e., to the left as shown in FIG. 1.

Dripping conditions produce droplets close to the entrance of collection tube 130 (FIG. 1) within a single orifice diameter; this can be analogized to a dripping faucet. Droplets produced by dripping are typically substantially monodisperse. By contrast, under jetting conditions, a long jet can be produced that extends three or more orifice diameters downstream into the collection tube, where it breaks into droplets. Although the distance from the opening may be greater under the jetting regime, droplets formed by either method are typically formed inside the collection tube. The jetting regime is typically quite irregular, resulting in polydisperse droplets, whose radius is much greater than that of the jet. Jet formation is believed to be caused by the viscous stress of the outer fluid on the middle fluid. When viscous effects dominate over inertial effects, the Reynolds number is low. The formation of multiple emulsions is similar to that of single emulsions; however, there are at least two fluids flowing coaxially, each of which can form droplets through either mechanism.

Droplet formation and morphology can be affected in a number of ways. For example, the geometry of the device, including the relationship of an outer conduit and two inner conduits, can be useful in developing multiple emulsions of desired size, frequency, and content. For example, the size of the orifice 162 and the inner taper of collection tube 130 can help to maintain three fluids in position, allowing droplets 180 to form. In addition, droplet formation can be affected by the rate of flow of the inner fluid, the rate of flow of the middle fluid, the rate of flow of the outer fluid, the total amount of flow or a change in the ratios, and/or combinations of any of these flow rates. In some embodiments, multiple droplets of inner fluid can be formed within a single droplet of the middle fluid. For example, 2, 3, 4, 5, 10, 30, 100, 300, 1000 or more droplets of inner fluid can be formed within a droplet of middle fluid by varying the frequency of droplet formation of either (or both) the inner fluid or the middle fluid, in relation to the other of the inner fluid or the middle fluid. For instance, if the velocity of the inner fluid is altered so that five droplets are formed over the same amount of time as a single droplet of middle fluid, then a droplet of middle fluid may contain, on average, five droplets of inner fluid. It should be noted that, depending on the fluid flow characteristics, some of the middle fluid droplets may contain more or fewer droplets of inner fluid, although the average is five droplets, as discussed in this example. As the absolute and relative flow rates of the three fluids can be carefully controlled using the devices described herein, the middle fluid droplets containing specific numbers of inner fluid droplets can be consistently and repeatedly formed. In some embodiments, the standard deviation from a target number of inner fluid droplets per middle fluid droplet may be, for example, less than one inner droplet, or less than about 20% of the number of inner droplets per middle fluid droplet. In other embodiments, the standard deviation may be, for example, less than about 15%, less than about 12%, less than about 10%, less than about 8%, or less than about 6% of the number of inner droplets per middle fluid droplet. In some cases, substantially all of the outer droplets will contain the same number of droplets therein.

The relative sizes of the inner fluid droplet and the middle fluid droplet can also be carefully controlled, i.e., the ratio of the size of the inner and outer droplets can be predicatively controlled. For instance, inner fluid droplets may fill much of or only a small portion of the middle fluid (outer) droplet. Inner fluid droplets may fill less than about 90%, less than about 80%, less than about 70%, less than about 60%, less than about 50%, less than about 30%, less than about 20%, or less than about 10% of the volume of the outer droplet. Alternatively, the inner fluid droplet may form greater than about 10%, about 20%, about 30%, about 40%, about 50%, about 60%, about 70%, about 90%, about 95%, or about 99% of the volume of the outer droplet. In some cases, the outer droplet can be considered a fluid shell, or coating, when it contains an inner droplet, as some or most of the outer droplet volume may be filled by the inner droplet. The ratio of the middle fluid shell thickness to the middle fluid droplet radius can be equal to or less than, e.g., about 5%, about 4%, about 3%, or about 2%. This can allow, in some embodiments, for the formation of multiple emulsions with only a very thin layer of material separating, and thus stabilizing, two miscible fluids. The middle shell material can also be thickened to greater than or equal to, e.g., about 10%, about 20%, about 30%, about 40%, or about 50% of the middle fluid droplet radius.

In some cases, such as when droplets of middle fluid 150 (outer droplets) are formed at the same rate as are droplets of inner fluid 140, then there is a one-to-one correspondence between inner fluid and middle fluid droplets, and each droplet of inner fluid is surrounded by a droplet of middle fluid, and each droplet of middle fluid contains a single inner droplet of inner fluid. The term "outer droplet," in this case, means a fluid droplet containing an inner fluid droplet that comprises a different fluid. In many embodiments that use three fluids for multiple emulsion production, the outer droplet is formed from a middle fluid and not from the outer (or carrying) fluid as the term may imply. It should be noted that the above-described figure and description is by way of example only, and other multiple emulsions (having differing numbers of nesting levels), and other devices are also contemplated within the instant invention. For example, the device in FIG. 1 may be modified to include additional concentric tubes, for example, to produce more highly nested droplets. Even higher degrees of nesting are possible, for example, 4 concentric tubes, 5 concentric tubes, or the like. It should be noted that "concentric," as used herein, does not necessarily refer to tubes that are strictly coaxial, but also includes nested or "off-center" tubes that do not share a common center line.

Figure 2A:
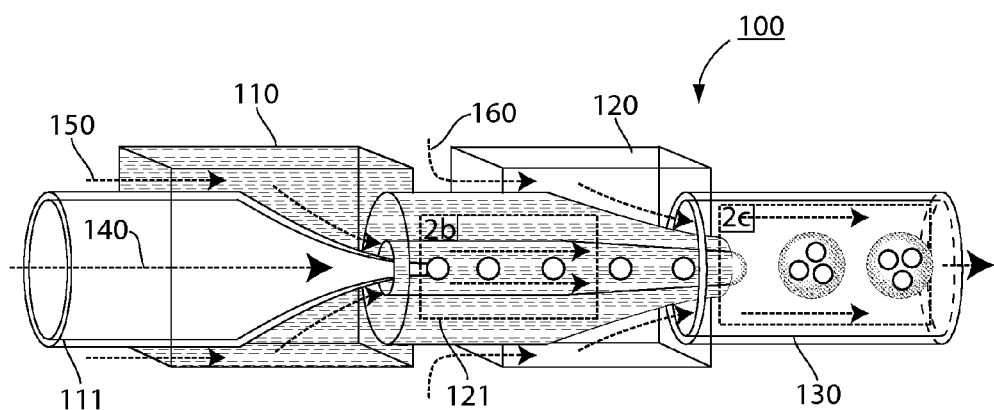
FIGS. 2A-2C illustrate another microfluidic device useful in making multiple emulsions, according to another embodiment of the invention.
Figure 2B:
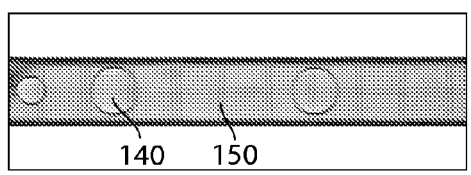

As another example, the device shown in FIG. 2A can also be used to produce a multiple emulsion. In this figure, device 100 includes a first conduit 110, containing injection tube 111, which ends in the interior of first conduit 110. As depicted, first conduit 110 has a generally rectangular cross-section while injection tube 111 has a generally circular or elliptical cross section; however, in other embodiments of the invention, some or all of these may have other cross-sectional shapes. Injection tube 111 contains inner fluid 140, while first conduit 110 contains middle fluid 150. Within first conduit 110, the fluids are passed into injection tube 121, and may form droplets of inner fluid 140 contained within middle fluid 150. An example of this is shown in FIG. 2B, which is a micrograph of an actual device, in use, having the configuration shown in FIG. 2A (the micrograph is of the region labeled in FIG. 2A as region "b"). As discussed below, the flow of middle fluid 150 may facilitate the reduction of the average diameter of the droplets of inner fluid 140 formed within the device in some cases.

Figure 2C:
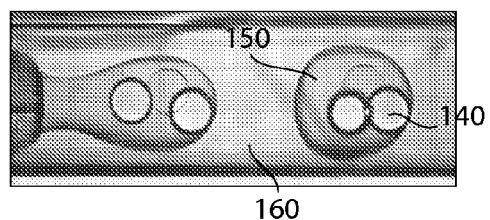

From injection tube 121, the inner and middle fluids pass into second conduit 120. Injection tube 121 ends in the interior of second conduit 120, which also contains outer fluid 160. Accordingly, outer fluid 160 enters second conduit 120 via a fluid path that does not enter first conduit 110. In FIG. 2A, second conduit 120 has a generally rectangular cross-section while injection tube 131 has a generally circular or elliptical cross section. In other embodiments of the invention, some or all of these may have other cross-sectional shapes. From second conduit 120, the fluids pass into tube 130, which also has a generally circular or elliptical cross section. Here, the middle fluid forms droplets contained within the outer fluid. As the middle fluid itself contains inner fluidic droplets, a triple emulsion is formed with one or more inner fluidic droplets contained within a middle fluidic droplet, which is contained within an outer fluid. As shown in FIG. 2C, which is a micrograph of an actual device in use (the micrograph is of the region labeled in FIG. 2A as region "c"), contained within outer fluid 160 is a fluidic droplet formed from middle fluid 150, containing three fluidic droplets formed from inner fluid 140. Of course, as discussed, more or fewer droplets of each fluid may be created, depending on the application. The rate of droplet formation for each fluidic droplet can be controlled by controlling the relative flowrates of each of the fluidic streams within the device, and/or the sizes of each of the tubes, conduits, etc., contained within the device.

Figure 5A:
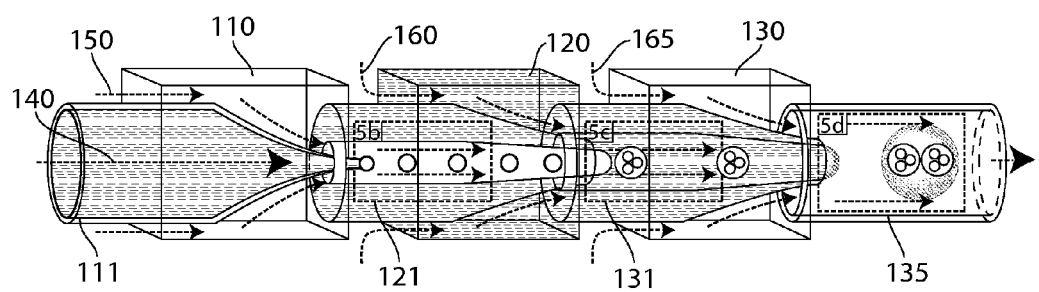
Figure 5B:
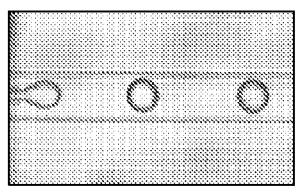
Figure 5C:
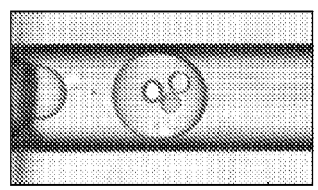
Figure 5D:
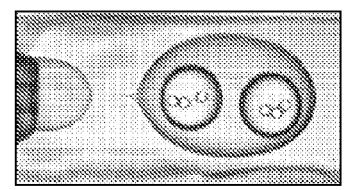
Figure 6A:
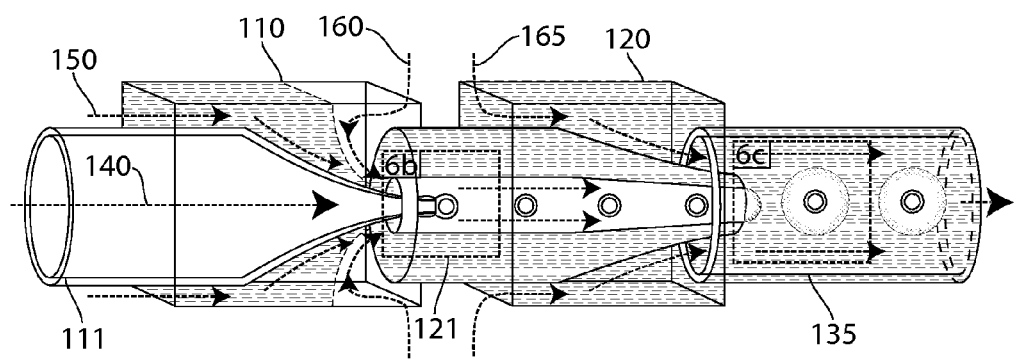
FIGS. 6A-6E illustrate still another microfluidic device useful in making multiple emulsions, according to another embodiment of the invention.
Figure 6B:
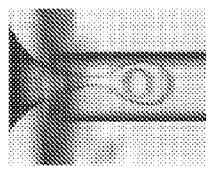
Figure 6C:
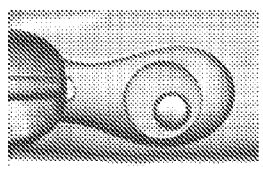
Figure 6D:
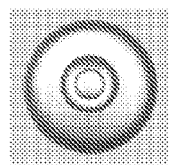
Figure 6E:
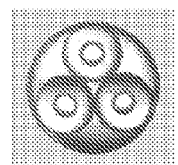

As another example, as shown in FIG. 5A, tube 131 extending from conduit 120 may be passed into conduit 130, in which a fourth fluid 165 is added, thereby producing a triple emulsion (i.e., one or more fluidic droplets, contained within one or more fluidic droplets, contained within one or more fluidic droplets, contained within a carrying fluid), which is collected within tube 135. Micrographs of the regions labeled "b," "c," and "d" in FIG. 5A are shown as FIGS. 5B, 5C, and 5D, respectively, illustrating the process by which a triple (or higher) emulsion can be formed, having varying numbers of droplets therein. FIG. 5E shows that, by controlling the relative flowrates of each of the fluidic streams within the device, emulsions having different numbers of various droplets therein can be formed, and in some cases, formed such that the plurality of droplets have substantially the same number of droplets formed therein. In addition, by controlling the relative flowrates, the average diameters of the droplets may also be controlled. If higher-order multiple emulsion droplets are desired, additional conduits can be added, e.g., in series. In addition, in some embodiments, a device having the configuration shown in FIG. 1 may also be combined with such a series of conduits, e.g., to create another nesting of droplets. An example of such a device is shown in FIG. 6A; FIGS. 6B and 6C show micrographs of the regions labeled "b," and "c" in FIG. 6A, showing the process by which a triple (or higher) emulsion can be formed. FIGS. 6D and 6E show micrographs of resultant multiple emulsions, having varying numbers of droplets therein.

The rate of production of multiple emulsion droplets may be determined by the droplet formation frequency, which under many conditions can vary between approximately 100 Hz and 5000 Hz. In some cases, the rate of droplet production may be at least about 200 Hz, at least about 300 Hz, at least about 500 Hz, at least about 750 Hz, at least about 1,000 Hz, at least about 2,000 Hz, at least about 3,000 Hz, at least about 4,000 Hz, or at least about 5,000 Hz.

In addition, by controlling the geometry of the conduits and the flow of fluid through the conduits, the average diameters of the droplets may be controlled, and in some cases, controlled such that the average diameter of the droplets is less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. Control of flow in such a fashion may be used to reduce the average diameters of the droplets in both single and multiple emulsions.

Figure 8A:
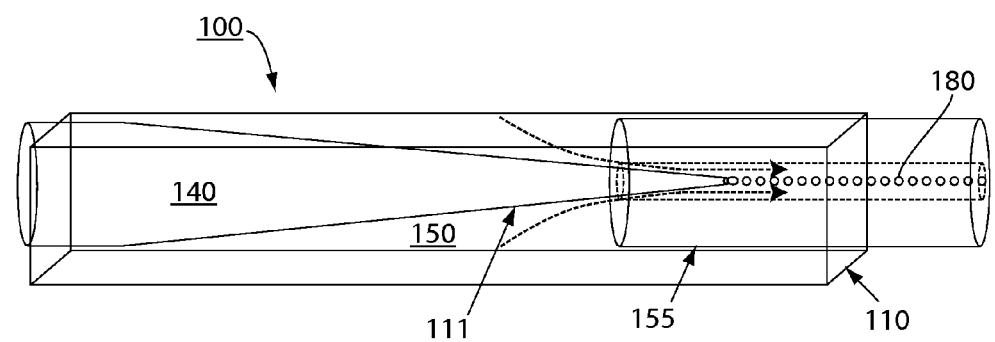
FIGS. 8A-8B illustrate microfluidic devices useful in making emulsions, according to another embodiment of the invention.

For instance, referring now to FIG. 8A, a portion of FIG. 2A is shown as an illustrative example. In this figure, device 100 includes first conduit 110 and injection tube 111. Conduit 110 is shown having two opposing ends or portions, but in reality, conduit 110 may be connected to other conduits, chambers, etc., within a microfluidic device. Injection tube 111 (carrying fluid 140) enters a first portion of conduit 110 but does not pass through the second portion of conduit 110 in FIG. 8A. Contained within conduit 110 is fluid 150, which may be immiscible with fluid 140 within injection tube 111. As depicted, first conduit 110 has a generally rectangular cross-section while injection tube 111 has a generally circular or elliptical cross section; however, in other embodiments of the invention, some or all of these may have other cross-sectional shapes. In addition, injection tube 111 may be tapered, as is shown in FIG. 8A, although it need not be. Also shown in FIG. 8A is conduit 155. Conduit 155 is shown passing through the second portion of first conduit 110, but not through the first portion. Conduits 155 and 111 are positioned such that the end of conduit 111 is positioned within conduit 155.

Figure 8B:
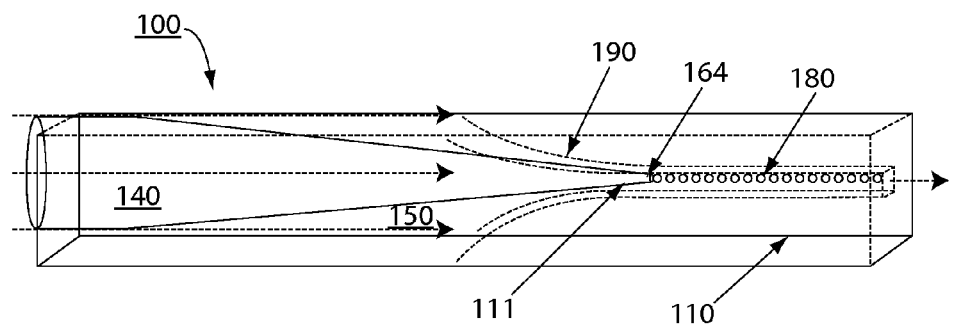

FIG. 8B shows another illustrative example. In FIG. 8B, device 100 includes first conduit 110 and injection tube 111. In this example, the inner cross-section of conduit 110 includes a tapered region 190. Injection tube 111 (carrying fluid 140) enters a first portion of conduit 110, and exit orifice 164 of injection tube 111 is disposed in a region of first conduit 110 with a smaller cross-sectional area than that of the entrance of first conduit 110. Injection tube 111 does not pass through the second portion of conduit 110. Fluid 150 is contained within conduit 110 and may be immiscible with fluid 140 within injection tube 111. As depicted, first conduit 110 has a generally rectangular cross-section while injection tube 111 has a generally circular or elliptical cross section; however, in other embodiments of the invention, some or all of these may have other cross-sectional shapes. In addition, injection tube 111 may be tapered, as is shown in FIG. 8B, although it need not be.

In some cases, the presence of conduit 155 may serve to accelerate the flow of fluid within conduit 110. Without wishing to be bound by any theory, it is believed that the smaller diameter of the fluid stream of fluid 140 travelling through conduit 155, relative to conduit 111, results in an increase in the flow rate of fluid through conduit 155, which results in smaller droplet formation. As shown in FIG. 8A, the smaller diameter results from the passage of both fluids 140 and 150 into conduit 155. This may be caused, for instance, by directing a fluid (which may be the same or different than fluid 150) into conduit 110 around conduit 155 such that the fluid passes into conduit 155 (see, e.g., FIG. 1), or by sealing the end of conduit 110 such that fluid cannot exit that end of conduit 110 except by passing through conduit 155, etc.

Production of large quantities of emulsions can be facilitated by the parallel use of multiple devices such as those described herein, in some instances. In some cases, relatively large numbers of devices may be used in parallel, for example at least about 10 devices, at least about 30 devices, at least about 50 devices, at least about 75 devices, at least about 100 devices, at least about 200 devices, at least about 300 devices, at least about 500 devices, at least about 750 devices, or at least about 1,000 devices or more may be operated in parallel. The devices may comprise different conduits (e.g., concentric conduits), orifices, microfluidics, etc. In some cases, an array of such devices may be formed by stacking the devices horizontally and/or vertically. The devices may be commonly controlled, or separately controlled, and can be provided with common or separate sources of various fluids, depending on the application.

In some embodiments of the invention, a droplet may be hardened, such as by using a fluid that can be solidified, gelled, and/or polymerized (e.g., to form a polymerosome). The droplet may be an outer droplet or one contained within a surrounding droplet. In some cases, capsules or spheres can be formed, i.e., by hardening a droplet containing one or more fluidic droplets therein. Any technique able to solidify a fluidic droplet can be used. For example, a fluidic droplet may be cooled to a temperature below the melting point or glass transition temperature of a fluid within the fluidic droplet, a chemical reaction may be induced that causes the fluidic droplet to solidify (for example, a polymerization reaction, a reaction between two fluids that produces a solid product, etc.), or the like. Other examples include pH-responsive or molecular-recognizable polymers, e.g., materials that gel upon exposure to a certain pH, or to a certain species.

In one embodiment, the fluidic droplet is solidified by reducing the temperature of the fluidic droplet to a temperature that causes at least one of the components of the fluidic droplet to reach a solid state. For example, the fluidic droplet may be solidified by cooling the fluidic droplet to a temperature that is below the melting point or glass transition temperature of a component of the fluidic droplet, thereby causing the fluidic droplet to become solid. As non-limiting examples, the fluidic droplet may be formed at an elevated temperature (i.e., above room temperature, about 25° C.), then cooled, e.g., to room temperature or to a temperature below room temperature; the fluidic droplet may be formed at room temperature, then cooled to a temperature below room temperature, or the like. As a specific example, a fluidic droplet may contain a gel such as a hydrogel, and the droplet may be solidified or hardened by cooling the droplet below its gelation temperature.

In some embodiments, this can be accomplished by a phase change in a fluid forming the droplet. A phase change can be initiated by a temperature change, for instance, and in some cases the phase change is reversible. For example, a wax or gel may be used as a fluid at a temperature which maintains the wax or gel as a fluid. Upon cooling, the wax or gel can form a solid or semisolid shell, e.g., resulting in a capsule or a hardened particle. In another embodiment, the shell can be formed by polymerizing the fluid. This can be accomplished in a number of ways, including using a pre-polymer that can be catalyzed, for example, chemically, through heat, or via electromagnetic radiation (e.g., ultraviolet radiation) to form a solid polymer shell or particle. In yet another embodiment, a gel may be formed by reacting two or more species together to form the gel, e.g., forming a solid or semisolid shell. As a specific example, two or more droplets or layers within droplets may contain different reactants, which can then mix or otherwise react to form a gel which can be one of the levels of encapsulation within a droplet.

In another aspect, the methods and apparatus of the invention can be used to form droplets containing species and to provide methods of delivering such species. For example, a specific fluidic droplet may be chosen to dissolve, rupture, or otherwise release its contents under certain conditions. Various species that can be contained within a fluidic droplet that can be released, for instance, cells, particles, pharmaceutical agents, drugs, DNA, RNA, proteins, etc., as discussed herein. For example, a fluidic droplet containing a drug (e.g., within an inner fluidic droplet) may be chosen to dissolve, rupture, etc. under certain physiological conditions (e.g., pH, temperature, osmotic strength), allowing the drug to be selectively released. The fluidic droplet may be an outer fluidic droplet (e.g., releasing its contents into a carrier fluid), or an inner fluidic droplet (e.g., releasing its contents into a surrounding fluidic droplet containing the droplet).

Any suitable method can be used to cause the fluidic droplet to release its contents. For example, the fluidic droplet may be subjected to a chemical reaction, which disrupts the droplet and causes it to release its contents. In some cases, the chemical reaction may be externally initiated (e.g., upon exposure by the droplet to light, a chemical, a catalyst, etc.). As another example, a fluidic droplet may comprise a temperature-sensitive material. In one set of embodiments, the temperature-sensitive material changes phase upon heating or cooling, which may disrupt the material and allow release to occur. In another set of embodiments, the temperature-sensitive material shrinks upon heating or cooling. In some cases, shrinking of the material may cause the fluidic droplet to decease in size, causing release of its contents. An example of this process is shown in FIGS. 5F-5J, which shows an outer droplet, containing a plurality of inner droplets, that shrinks with a rise in temperature, eventually reaching the point where it no longer can contain inner droplets, which are then released. In some cases, a temperature change of at least about 10° C. or at least about 20° C. may be sufficient to cause release to occur.

A variety of materials and methods, according to certain aspects of the invention, can be used to form systems (such as those described above) able to produce the multiple droplets described herein. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device. A non-limiting example of such a coating is disclosed below; additional examples are disclosed in a U.S. provisional application filed on even date herewith, entitled "Surfaces, Including Microfluidic Channels, With Controlled Wetting Properties," by Weitz, et al., incorporated herein by reference.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric, and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy, et al.), incorporated herein by reference.

In some embodiments, certain microfluidic structures of the invention (or interior, fluid-contacting surfaces) may be formed from certain oxidized silicone polymers. Such surfaces may be more hydrophilic than the surface of an elastomeric polymer. Such hydrophilic channel surfaces can thus be more easily filled and wetted with aqueous solutions.

In one embodiment, a bottom wall of a microfluidic device of the invention is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, bonding, solvent bonding, ultrasonic welding, etc.

As mentioned, in one aspect of the invention, a surface of a microfluidic channel may be modified to facilitate the production of emulsions such as multiple emulsions. In some cases, the surface may be modified by coating a sol-gel onto at least a portion of a microfluidic channel. As is known to those of ordinary skill in the art, a sol-gel is a material that can be in a sol or a gel state, and typically includes polymers. The gel state typically contains a polymeric network containing a liquid phase, and can be produced from the sol state by removing solvent from the sol, e.g., via drying or heating techniques. In some cases, as discussed below, the sol may be pretreated before being used, for instance, by causing some polymerization to occur within the sol.

In some embodiments, the sol-gel coating may be chosen to have certain properties, for example, having a certain hydrophobicity. The properties of the coating may be controlled by controlling the composition of the sol-gel (for example, by using certain materials or polymers within the sol-gel), and/or by modifying the coating, for instance, by exposing the coating to a polymerization reaction to react a polymer to the sol-gel coating, as discussed below.

For example, the sol-gel coating may be made more hydrophobic by incorporating a hydrophobic polymer in the sol-gel. For instance, the sol-gel may contain one or more silanes, for example, a fluorosilane (i.e., a silane containing at least one fluorine atom) such as heptadecafluorosilane, or other silanes such as methyltriethoxy silane (MTES) or a silane containing one or more lipid chains, such as octadecylsilane or other $CH_3(CH_2)_n$— silanes, where n can be any suitable integer. For instance, n may be greater than 1, 5, or 10, and less than about 20, 25, or 30. The silanes may also optionally include other groups, such as alkoxide groups, for instance, octadecyltrimethoxysilane. In general, most silanes can be used in the sol-gel, with the particular silane being chosen on the basis of desired properties such as hydrophobicity. Other silanes (e.g., having shorter or longer chain lengths) may also be chosen in other embodiments of the invention, depending on factors such as the relative hydrophobicity or hydrophilicity desired. In some cases, the silanes may contain other groups, for example, groups such as amines, which would make the sol-gel more hydrophilic. Non-limiting examples include diamine silane, triamine silane, or N-[3-(trimethoxysilyl)propyl]ethylene diamine silane. The silanes may be reacted to form oligomers or polymers within the sol-gel, and the degree of polymerization (e.g., the lengths of the oligomers or polymers) may be controlled by controlling the reaction conditions, for example by controlling the temperature, amount of acid present, or the like. In some cases, more than one silane may be present in the sol-gel. For instance, the sol-gel may include fluorosilanes to cause the resulting sol-gel to exhibit greater hydrophobicity, and other silanes (or other compounds) that facilitate the production of polymers. In some cases, materials able to produce $SiO_2$ compounds to facilitate polymerization may be present, for example, TEOS (tetraethyl orthosilicate).

It should be understood that the sol-gel is not limited to containing only silanes, and other materials may be present in addition to, or in place of, the silanes. For instance, the coating may include one or more metal oxides, such as $SiO_2$, vanadia ($V_2O_5$), titania ($TiO_2$), and/or alumina ($Al_2O_3$).

In some instances, the microfluidic channel is constructed from a material suitable to receive the sol-gel, for example, glass, metal oxides, or polymers such as polydimethylsiloxane (PDMS) and other siloxane polymers. For example, in some cases, the microfluidic channel may be one in which contains silicon atoms, and in certain instances, the microfluidic channel may be chosen such that it contains silanol (Si—OH) groups, or can be modified to have silanol groups. For instance, the microfluidic channel may be exposed to an oxygen plasma, an oxidant, or a strong acid cause the formation of silanol groups on the microfluidic channel.

The sol-gel may be present as a coating on the microfluidic channel, and the coating may have any suitable thickness. For instance, the coating may have a thickness of no more than about 100 micrometers, no more than about 30 micrometers, no more than about 10 micrometers, no more than about 3 micrometers, or no more than about 1 micrometer. Thicker coatings may be desirable in some cases, for instance, in applications in which higher chemical resistance is desired. However, thinner coatings may be desirable in other applications, for instance, within relatively small microfluidic channels.

In one set of embodiments, the hydrophobicity of the sol-gel coating can be controlled, for instance, such that a first portion of the sol-gel coating is relatively hydrophobic, and a second portion of the sol-gel coating is relatively hydrophobic. The hydrophobicity of the coating can be determined using techniques known to those of ordinary skill in the art, for example, using contact angle measurements such as those discussed below. For instance, in some cases, a first portion of a microfluidic channel may have a hydrophobicity that favors an organic solvent to water, while a second portion may have a hydrophobicity that favors water to the organic solvent.

The hydrophobicity of the sol-gel coating can be modified, for instance, by exposing at least a portion of the sol-gel coating to a polymerization reaction to react a polymer to the sol-gel coating. The polymer reacted to the sol-gel coating may be any suitable polymer, and may be chosen to have certain hydrophobicity properties. For instance, the polymer may be chosen to be more hydrophobic or more hydrophilic than the microfluidic channel and/or the sol-gel coating. As an example, a hydrophilic polymer that could be used is poly (acrylic acid).

The polymer may be added to the sol-gel coating by supplying the polymer in monomeric (or oligomeric) form to the sol-gel coating (e.g., in solution), and causing a polymerization reaction to occur between the polymer and the sol-gel. For instance, free radical polymerization may be used to cause bonding of the polymer to the sol-gel coating. In some embodiments, a reaction such as free radical polymerization may be initiated by exposing the reactants to heat and/or light, such as ultraviolet (UV) light, optionally in the presence of a photoinitiator able to produce free radicals (e.g., via molecular cleavage) upon exposure to light. Those of ordinary skill in the art will be aware of many such photoinitiators, many of which are commercially available, such as Irgacur 2959 (Ciba Specialty Chemicals) or 2-hydroxy-4-(3-triethoxysilylpropoxy)-diphenylketone (SIH6200.0, ABCR GmbH & Co. KG).

The photoinitiator may be included with the polymer added to the sol-gel coating, or in some cases, the photoinitiator may be present within the sol-gel coating. For instance, a photoinitiator may be contained within the sol-gel coating, and activated upon exposure to light. The photoinitiator may also be conjugated or bonded to a component of the sol-gel coating, for example, to a silane. As an example, a photoinitiator such as Irgacur 2959 may be conjugated to a silane-isocyanate via a urethane bond (where a primary alcohol on the photoinitiator may participate in nucleophilic addition with the isocyanate group, which may produce a urethane bond).

It should be noted that only a portion of the sol-gel coating may be reacted with a polymer, in some embodiments of the invention. For instance, the monomer and/or the photoinitiator may be exposed to only a portion of the microfluidic channel, or the polymerization reaction may be initiated in only a portion of the microfluidic channel. As a particular example, a portion of the microfluidic channel may be exposed to light, while other portions are prevented from being exposed to light, for instance, by the use of masks or filters. Accordingly, different portions of the microfluidic channel may exhibit different hydrophobicities, as polymerization does not occur everywhere on the microfluidic channel. As another example, the microfluidic channel may be exposed to UV light by projecting a de-magnified image of an exposure pattern onto the microfluidic channel. In some cases, small resolutions (e.g., 1 micrometer, or less) may be achieved by projection techniques.

Another aspect of the present invention is generally directed at systems and methods for coating such a sol-gel onto at least a portion of a microfluidic channel. In one set of embodiments, a microfluidic channel is exposed to a sol, which is then treated to form a sol-gel coating. In some cases, the sol can also be pretreated to cause partial polymerization to occur. Extra sol-gel coating may optionally be removed from the microfluidic channel. In some cases, as discussed, a portion of the coating may be treated to alter its hydrophobicity (or other properties), for instance, by exposing the coating to a solution containing a monomer and/or an oligomer, and causing polymerization of the monomer and/or oligomer to occur with the coating.

The sol may be contained within a solvent, which can also contain other compounds such as photoinitiators including those described above. In some cases, the sol may also comprise one or more silane compounds. The sol may be treated to form a gel using any suitable technique, for example, by removing the solvent using chemical or physical techniques, such as heat. For instance, the sol may be exposed to a temperature of at least about 150° C., at least about 200° C., or at least about 250° C., which may be used to drive off or vaporize at least some of the solvent. As a specific example, the sol may be exposed to a hotplate set to reach a temperature of at least about 200° C. or at least about 250° C., and exposure of the sol to the hotplate may cause at least some of the solvent to be driven off or vaporized. In some cases, however, the sol-gel reaction may proceed even in the absence of heat, e.g., at room temperature. Thus, for instance, the sol may be left alone for a while (e.g., about an hour, about a day, etc.), and/or air or other gases may be passed over the sol, to allow the sol-gel reaction to proceed.

In some cases, any ungelled sol that is still present may be removed from the microfluidic channel. The ungelled sol may be actively removed, e.g., physically, by the application of pressure or the addition of a compound to the microfluidic channel, etc., or the ungelled sol may be removed passively in some cases. For instance, in some embodiments, a sol present within a microfluidic channel may be heated to vaporize solvent, which builds up in a gaseous state within the microfluidic channels, thereby increasing pressure within the microfluidic channels. The pressure, in some cases, may be enough to cause at least some of the ungelled sol to be removed or "blown" out of the microfluidic channels.

In certain embodiments, the sol is pretreated to cause partial polymerization to occur, prior to exposure to the microfluidic channel. For instance, the sol may be treated such that partial polymerization occurs within the sol. The sol may be treated, for example, by exposing the sol to an acid or temperatures that are sufficient to cause at least some gellation to occur. In some cases, the temperature may be less than the temperature the sol will be exposed to when added to the microfluidic channel. Some polymerization of the sol may occur, but the polymerization may be stopped before reaching completion, for instance, by reducing the temperature. Thus, within the sol, some oligomers may form (which may not necessarily be well-characterized in terms of length), although full polymerization has not yet occurred. The partially treated sol may then be added to the microfluidic channel, as discussed above.

In certain embodiments, a portion of the coating may be treated to alter its hydrophobicity (or other properties) after the coating has been introduced to the microfluidic channel. In some cases, the coating is exposed to a solution containing a monomer and/or an oligomer, which is then polymerized to bond to the coating, as discussed above. For instance, a portion of the coating may be exposed to heat or to light such as ultraviolet right, which may be used to initiate a free radical polymerization reaction to cause polymerization to occur. Optionally, a photoinitiator may be present, e.g., within the sol-gel coating, to facilitate this reaction.

The following applications are each incorporated herein by reference: U.S. patent application Ser. No. 08/131,841, filed Oct. 4, 1993, entitled "Formation of Microstamped Patterns on Surfaces and Derivative Articles," by Kumar, et al., now U.S. Pat. No. 5,512,131, issued Apr. 30, 1996; U.S. patent application Ser. No. 09/004,583, filed Jan. 8, 1998, entitled "Method of Forming Articles including Waveguides via Capillary Micromolding and Microtransfer Molding," by Kim, et al., now U.S. Pat. No. 6,355,198, issued Mar. 12, 2002; International Patent Application No. PCT/US96/03073, filed Mar. 1, 1996, entitled "Microcontact Printing on Surfaces and Derivative Articles," by Whitesides, et al., published as WO 96/29629 on Jun. 26, 1996; International Patent Application No.: PCT/US01/16973, filed May 25, 2001, entitled "Microfluidic Systems including Three-Dimensionally Arrayed Channel Networks," by Anderson, et al., published as WO 01/89787 on Nov. 29, 2001; U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," by Stone, et al., published as U.S. Patent Application Publication No. 2005/0172476 on Aug. 11, 2005; International Patent Application No. PCT/US2006/007772, filed Mar. 3, 2006, entitled "Method and Apparatus for Forming Multiple Emulsions," by Weitz, et al., published as WO 2006/096571 on Sep. 14, 2006; U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007; and U.S. patent application Ser. No. 11/368,263, filed Mar. 3, 2006, entitled "Systems and Methods of Forming Particles," by Garstecki, et al. Also incorporated herein by reference are U.S. Provisional Patent Application Ser. No. 60/920,574, filed Mar. 28, 2007, entitled "Multiple Emulsions and Techniques for Formation," by Chu, et al., and a U.S. provisional application filed on even date herewith, entitled "Surfaces, Including Microfluidic Channels, With Controlled Wetting Properties," by Weitz, et al., incorporated herein by reference.

The following examples are intended to illustrate certain embodiments of the present invention, but do not exemplify the full scope of the invention.

EXAMPLE 1

This example illustrates a microfluidic technique for producing various multiple emulsions. FIG. 2 shows a schematic illustration of the coaxial capillary microfluidic device used for fabricating substantially monodisperse double emulsions with controllable size and number of droplets contained therein. As shown in this figure, the microfluidic device used in this example included cylindrical glass capillary tubes nested within square glass capillary tubes. Details of this device are given below. The outer diameter of the round tubes was approximately the same as the inner dimension of the square tubes, so that the alignment of the device had a generally coaxial geometry. To prepare double emulsions, the innermost fluid was pumped through a tapered round microcapillary tube, and the middle fluid was pumped through the outer coaxial region between the injection tube and the left square tube, which formed a coaxial flow in the transition tube. The inner fluid broke into droplets at the orifice of the injection tube (see FIG. 2B, which is an optical micrograph), which were single emulsions. The outermost fluid was pumped through the outer coaxial region between the transition tube and the right square tube, and formed a coaxial flow in the collection tube with the single emulsion solution from the transition tube. Again, the solution containing single emulsion droplets broke into drops at the orifice of the transition tube (FIG. 2C), resulting in double emulsions. The size of single emulsion and double emulsion droplets could be tuned by adjusting the solution chemophysical properties, flowrates, and/or the transition and collection tube diameters. The number of droplets contained inside the double emulsions could be controlled by tuning the ratio of drop-formation frequency of single emulsions to that of double emulsions, which could be simply achieved by changing flowrates. The emulsifications of both single emulsions and double emulsions were operated in dripping regimes, and control of droplet size and drop-formation frequency was found to be easy and stable. As a result, not only the diameter of double emulsions but also the number and size of the droplets contained inside double emulsions could be controlled. In addition, no wetting problems appear to exist during drop formation; in other words, no surface modification was needed for the device, and the same device could be used to prepare both w/o/w (water/oil/water) and o/w/o (oil/water/oil) double emulsions by merely changing solutions.

Figure 3A:
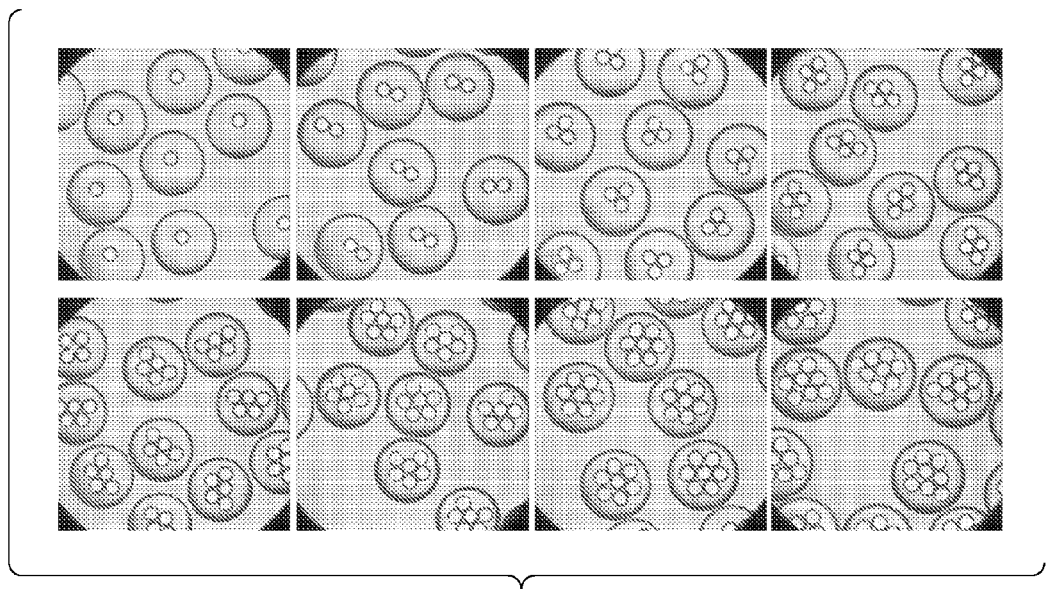
FIGS. 3A-3B illustrate various multiple emulsions, produced using various embodiments of the invention.
Figure 3B:
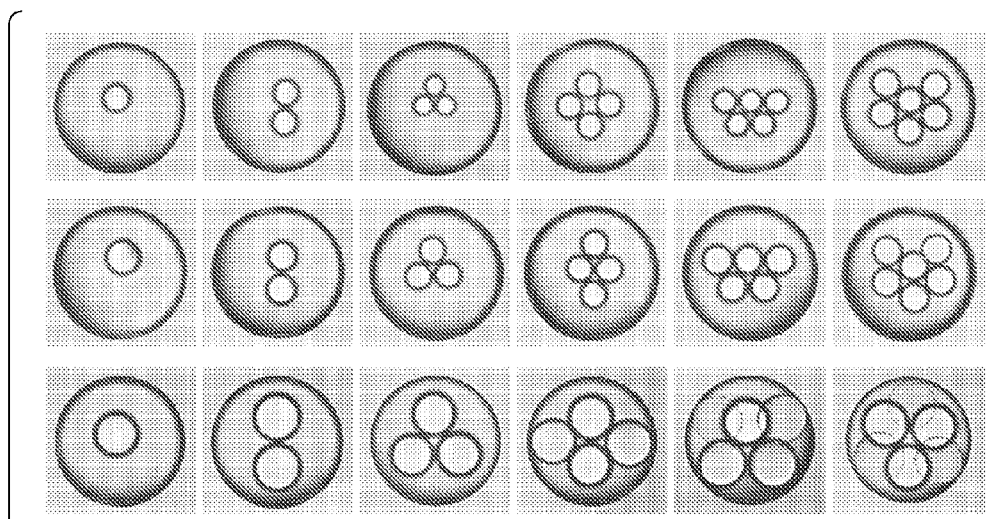

FIG. 3 shows optical micrographs of substantially monodisperse double emulsions with controllable numbers and sizes of droplets. FIG. 3A shows substantially monodisperse double emulsions having different number of droplets contained therein, while FIG. 3B shows that substantially monodisperse double emulsions where the ratio of the diameters of inner droplets to outer droplet could be tuned by adjusting the flowrates of the fluids. The scale bar in these figures is 200 micrometers. Both the outer diameter of the double emulsions and the diameter of internal droplets were substantially monodisperse. All of these emulsions were made in the same device and with the same solution system. By changing the flowrates, the number of contained droplets could be tuned gradually from 1 to 8 or more (not shown in the figure), with substantially the same number of droplets in each. For each number of contained droplets, the diameter ratio of the inner drop to the double emulsion could be controlled by adjusting the solution flowrates and chemphysical properties. The diameter ratio of the internal droplet to double emulsion could be made larger than that shown in FIG. 3, for example, simply by increasing the flowrate of inner fluid or that of outer fluid, and/or decreasing that of middle fluid.

Figure 4A:
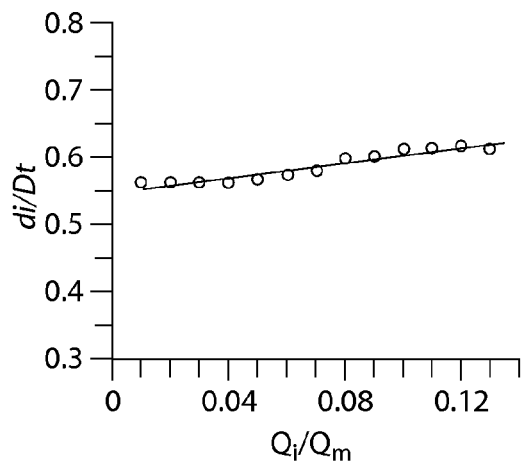
FIGS. 4A-4C illustrate data indicating control over droplet formation and nesting, in accordance with one embodiment of the invention.
Figure 4B:
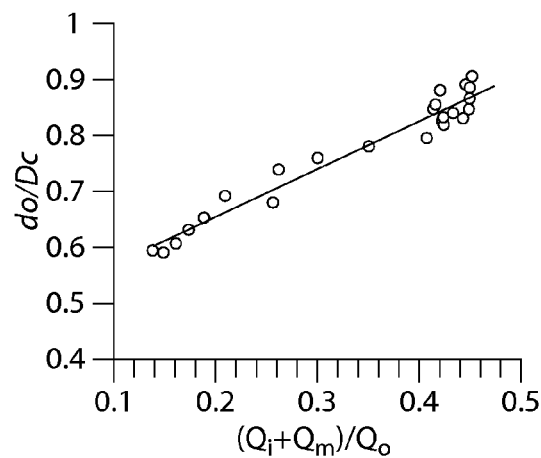

Without wishing to be bound by any theory, it is believed that the number of droplets can be predicted as follows. Because the drop formation in the microfluidic device was operated in dripping regimes, for a fixed solution system, the diameter ratio of droplet to tube may be controlled to be proportional to the flowrate ratio of disperse phase to continuous phase, as shown in FIGS. 4A and 4B, in which $d_i$, $d_o$, $D_t$ and $D_c$ are respectively diameters of internal droplet, multiple emulsion, transition tube and collection tube, and $Q_i$, $Q_m$ and $Q_o$ are flowrates of inner, middle and outer fluids respectively. In particular, FIG. 4A shows the ratio of the diameters of single emulsion droplets ($d_i$) to that of the transition tube ($D_t$) as a function of the relative flowrates of the inner ($Q_i$) and middle fluid ($Q_m$). In this case, $D_t$ was held constant at 200 micrometers. FIG. 4B shows the ratio of the diameters of the double emulsion droplets ($d_o$) to that of the collection tube ($D_c$) as a function of the flowrates of the inner ($Q_i$), middle ($Q_m$), and outer ($Q_o$) fluids. In this case, $D_c$ was held constant at 580 micrometers.

By using the linear relationships illustrated in FIGS. 4A and 4B, the number of droplets contained inside double emulsions can be estimated as:

$$N_i = \frac{f_i}{f_o} = \frac{\frac{Q_i}{\pi d_i^3/6}}{\frac{Q_i+Q_m}{\pi d_o^3/6}} = \frac{Q_i}{Q_i+Q_m} \cdot \frac{D_c^3}{D_t^3} \cdot \left(\frac{a_o\left(\frac{Q_i+Q_m}{Q_o}\right)+b_o}{a_i\left(\frac{Q_i}{Q_m}\right)+b_i}\right)^3 \quad (1)$$

where $N_i$ is the number of contained droplets, $f_i$ and $f_o$ are generation frequencies of single and double emulsions, and $a_i$, $b_i$, $a_o$, and $b_o$ are constants that can be obtained from FIGS. 4A and 4B. For a fixed device dimension and fixed solutions in a coaxial flow system, if the drop formation is controlled in the dripping regime, the droplet diameter should be approximately inversely proportional to the flowrate of continuous phase. Therefore, the number $N_i$ should be proportional to $(Q_i/(Q_i+Q_m))(Q_m/Q_o)^3$.

Figure 4C:
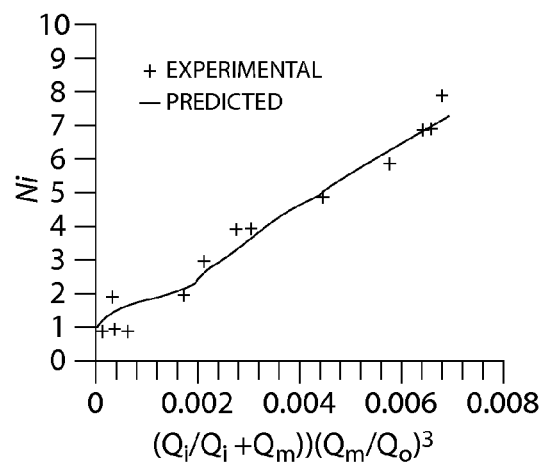

FIG. 4C shows theoretical predictions and experimental data displaying the dependence of the number of droplets contained inside double emulsions on the relative flowrates of the three fluids. The predicted numbers of the contained droplets by Equation 1 generally fit the experimental data. Thus, a device can be designed with suitable tube diameters and operated with suitable flowrates according to desired sizes of internal droplets and double emulsions and desired numbers of contained droplets, using the strategies outlined above, without an undue amount of experimentation.

This microfluidic device can also be readily extended to prepare triple or higher multiple emulsions. For instance, FIG. 5 shows triple emulsions that were generated from a coaxial capillary microfluidic device by adding another emulsification stage between the transition tube and collection tube shown in FIG. 2A. Thus, using similar principles, substantially monodisperse triple emulsions can be obtained. The device is schematically shown in FIG. 5A, while FIGS. 5B, 5C, and 5D show the emulsification processes for single, double, or triple emulsions respectively, within the device. During the formation of triple emulsions, flexible deformation of the droplets of double emulsions was observed, although the droplets remained were stable in the triple emulsions. FIG. 5E shows that both the size and number of single emulsions in double emulsions and that of double emulsions in triple emulsions could be tuned simultaneously to any desired number, using the methods discussed above. Although the structure of multiple emulsions becomes more complex, control is still stable and substantially all of the droplets produced had substantially the same number of droplets.

The following describes, in greater detail, some of the techniques used in this example. For preparing double emulsions, the carrying fluid was poly(dimethylsiloxane) oil (100 cSt, Sigma-Aldrich) containing 2 wt % of Dow Corning 749 fluid (Dow Corning), the outer fluid (forming the droplet) was an aqueous solution containing 2% (w/v) of poly(vinyl alcohol) (PVA, 87-89% hydrolyzed, Sigma-Aldrich) and 10 wt % glycerol (Sigma-Aldrich), and the inner fluid (forming droplets within the outer fluid) was poly(dimethylsiloxane) oil (10 cSt, Sigma-Aldrich).

For preparing triple emulsions, the carrying fluid and the outer fluid were the same as the carrying fluid and the outer fluid in the preparation of double emulsions, the first fluid (numbering inward from the outer fluid) was kerosene (Sigma-Aldrich) containing 10% (w/v) of polyglycerol polyricinoleate (PGPR 90, Danisco) and 15 wt % of Dow Corning 749 fluid, and the second (innermost) fluid was the same as the outer fluid. For preparing the thermo-sensitive microcapsule from the triple emulsions, the carrying fluid and the second (innermost) fluid were the same as the above triple emulsion. The outer fluid was aqueous solution containing 2% (w/v) of PVA, 10 wt % of glycerol, 11.3% (w/v) of monomer N-isopropylacrylamide (NIPAM, 99%, Acros), 0.8% (w/v) of co-monomer sodium acrylate (Sigma-Aldrich), 0.77% (w/v) of crosslinker N,N'-methylenebisacryamide (BIS, Sigma-Aldrich), and 0.6% (w/v) of initiator ammonium persulfate (APS, Acros). The first fluid was poly (dimethylsiloxane) oil (10 cSt) containing 5 wt % of Dow Corning 749 fluid and 8% (v/v) of accelerator N,N,N',N'-tetramethylethylenediamine (TEMED, 99%, Acros).

The microfluidic devices were prepared as follows. Borosilicate glass tubes were assembled on microscope slide glasses. The outer diameters of round tubes were 1.0 mm, which is the inner dimension of square tubes (VitroCom). The inner diameter of the transition tube for preparing double emulsions was 200 micrometers (AIT glass), and those of the other transition tubes for preparing triple emulsions were 100 micrometers and 250 micrometers, respectively (AIT glass). The inner diameter of the final (collection) tube was 580 micrometers (VitroCom). No surface modifications were made for the glass tubing. The spaces between right ends of the square tubes and the round tubes in FIG. 2A and FIG. 5A were sealed by transparent epoxy resin. The microfluidic device was mounted on a microscope stage (Leica, DMIRBE). The solutions were supplied to the microfluidic device through polyethylene tubing (Scientific Commodities) attached to syringes (Hamilton Gastight) operated by syringe pumps (Harvard Apparatus, PHD 2000 series). A Phantom high-speed camera (Vision Research) was used to record the drop formation processes.

EXAMPLE 2

The control over the structure of the multiple emulsions shown here not only improves the emulsion performance and promotes their applications, but also enables the fabrication of new functional materials. For example, by using the double emulsions as templates, microcapsules or microspheres can be created with controllable pores or smaller microspheres with different materials inside, or non-spherical particles can be prepared through the three-dimensional assemblies of droplets inside the emulsions. Using the triple emulsions, more complicated systems can be prepared, e.g., microcapsules or microspheres with multiple layers of functional materials, and/or with smaller functional particles contained therein, and/or with both oil-soluble and water-soluble functional substances encapsulated inside, etc.

As an example, a thermo-sensitive hydrogel microcapsule for pulsed release was prepared from made from a w/o/w/o emulsion. However, besides thermo-sensitive hydrogel materials, other stimuli-responsive polymers could be used, e.g., pH-responsive or molecular-recognizable polymers. Environmental stimuli-sensitive polymeric hydrogel materials have attracted a widespread interest due to their potential applications in numerous fields. Much attention has been recently focused on thermo-responsive hydrogel systems. The fabrication of thermo-sensitive functional systems is of both scientific and technological interest. In this example, a droplet having a hydrogel shell was prepared containing a poly(N-isopropylacrylamide)-based hydrogel. Monomer, crosslinker, and initiator were added to one fluid, while an accelerator was added to another fluid. Polymerization was initiated by redox reaction. As shown in FIG. 5F, which is an optical micrograph of a representative thermo-sensitive microcapsule, the microcapsules were prepared having a thermo-sensitive hydrogel shell and a complex liquid core (oil phase containing certain number of aqueous droplets).

FIGS. 5F-5J are optical snapshots displaying the pulsed release process from such a thermo-sensitive microcapsule when the system temperature was increased from 25° C. to 50° C. The gradually developing shaded area surrounding the shrinking microcapsule is the aqueous solution which was released from the microgel shell. The scale bar in all of these figures is 200 micrometers. When the environmental temperature was changed, the poly(N-isopropylacrylamide)-based hydrogel shell shrank rapidly (FIGS. 5G and 5H). Because the volume of liquid core could not be compressed, when the shrinkage of the outer layer reached a certain point, the internal oil phase, together with the aqueous droplets were released from the microcapsule (FIGS. 5I and 5J). The pulsed release behavior of the microcapsule made it function as a thermo-sensitive hydrogel "Trojan Horse," which could be used, for example, for the controlled pulse release of drugs or other substances.

Polymerization and characterization of thermo-sensitive microcapsules is as follows. TEMED is both oil-soluble and water-soluble. When the accelerator TEMED in the first fluid diffuses outwardly into the outer fluid and meets the initiator APS, a redox reaction is initiated that can polymerize the monomers. The polymerized microcapsules, together with surrounding solution, were put into a transparent holder on the slide glass, which was put on a heating and cooling stage of a microscope (Physitemp Instruments, TS-4ER), to test the thermo-sensitive pulsed release. A digital camera (Hamamatsu, C4742-95) is used to record the thermo-responsive behavior and the pulsed release process of microcapsules.

EXAMPLE 3

Due to their thermodynamically unfavorable nature, emulsions do not form spontaneously. Energy input through shaking, stirring, homogenizers, or spray processes are often used to form an emulsion. Most conventional emulsification techniques involve bulk mixing of the dispersed phase and the continuous phase. These techniques are used widely in an industrial scale to produce different emulsion formulations. However, many of these techniques use turbulence to enhance drop breakup. In these "top-down" approaches to emulsification, little control over the formation of individual droplets is available, and a broad distribution of sizes is typically produced. For applications that require monodisperse emulsion with a narrow droplet size distribution, an additional fractionation step is required, but the method is time-consuming and inefficient because the bulk of the dispersed phase is not used.

This example illustrates the formation of monodisperse emulsions in a microfluidic channel using a "bottom-up" approach. This technique uses coaxial flow and hydrodynamically focused flow to generate emulsion droplets one-by-one in a controlled fashion. In particular, this example illustrates the making of smaller monodisperse droplets in a three dimensional microfluidic emulsification device, e.g., droplets having an average diameter of less than about 10 micrometers.

Figure 7:
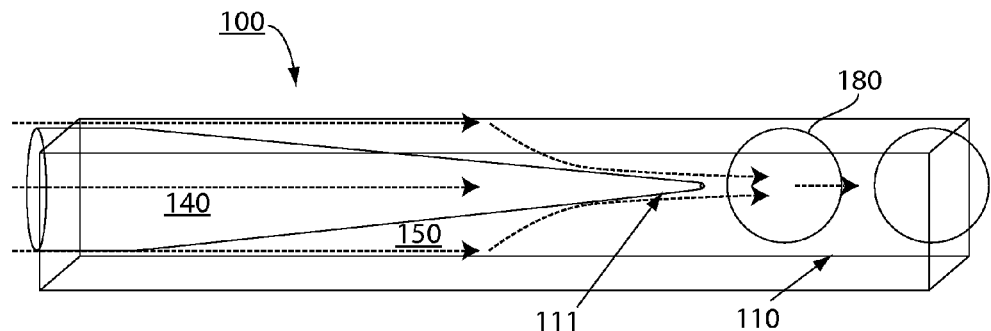
FIG. 7 illustrates a microfluidic device useful in making emulsions, according to one embodiment of the invention.

One method of making an emulsion inside a microfluidic channel is to position an injection tube 111 inside collection tube 110, as shown in FIG. 7. In this microfluidic device, a first liquid 140 flows into a second, immiscible liquid 150 to make an emulsion of droplets 180 of the first liquid in the second liquid. The diameter of the liquid-liquid emulsion droplets generated in this particular example is a function of factors such as the injection tube diameter, the viscosity of the continuous phase, and/or its velocity at the exit of the injection tube. For instance, for a fixed continuous phase viscosity, the higher the velocity of the continuous phase at the injection tube exit is, the smaller the possible emulsion droplet diameter is. The continuous phase mean velocity, $V_{continuous}$, is determined in this particular example by the flow rate, $Q_{continuous}$, of the continuous phase and the cross-sectional area, $A_{collection}$, of the collection tube, according to Eq. 2:

$$v_{continuous} = \frac{Q_{continuous}}{A_{collection}}. \quad (2)$$

As shown in FIG. 7, the injection tube may be tapered to achieve smaller droplets. In order to fit the injection tube inside the collection tube, the area, $A_{collection}$, of the collection tube has to be at least slightly larger than that of the untapered region of the injection tube. As a result, the collection tube area, $A_{collection}$, cannot be reduced easily. Therefore, when smaller droplets are desired, the flow rate of the continuous phase, $Q_{continuous}$, is often increased.

Another embodiment of the invention is shown in FIG. 8A. In this embodiment, a flow acceleration tube 155 has been included relative to FIG. 7. With the flow acceleration tube, in this particular example, the area of the channel, equivalent to $A_{collection}$, is no longer limited by that of the untapered region of the injection tube. Since the tube area $A_{collection}$ scales with the square of its diameter, putting the injection tube inside a flow acceleration tube with half the diameter quadruples the continuous phase velocity, $v_{continuous}$, for a given flow rate $Q_{continuous}$. The inclusion of the flow acceleration tube therefore allows the generation of smaller emulsion droplets in this particular case. Moreover, it also increases the volume fraction of emulsion droplets by reducing the flow rate of continuous phase required for a given droplet size. By reducing the flow rate of continuous phase required per emulsion droplet in this example, the flow acceleration tube increases the number of droplets produced per run, thus reducing the frequency of continuous phase refilling.

Figure 9:
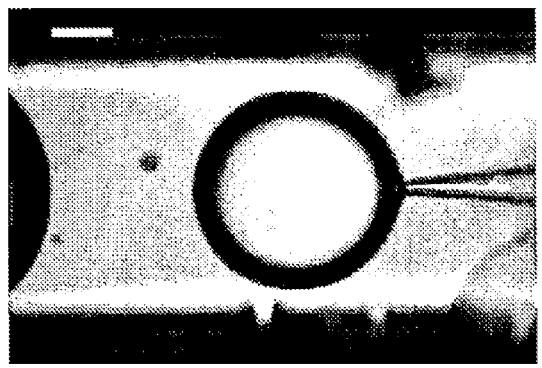
FIG. 9 is a photomicrograph of an emulsion produced using one embodiment of the invention.

Preliminary experiments showed that with a regular three-dimensional microfluidic device as discussed above, at a continuous phase flow rate of 25 mL/hr, the droplets generated had a size of 900 micrometers. The droplet was formed from dodecane in an aqueous solution of 8 mM sodium dodecyl sulfate (SDS). The collection tube width was 1 mm and the injection tube diameter was 8 micrometers. The scale bar has a length of 200 micrometers. The cross-sectional area of the collection tube was $10^6$ micrometers$^2$. By incorporating the flow acceleration tube, which has a cross-sectional area of 7900 micrometers$^2$, the velocity of the continuous phase at the exit of the injection tube was increased to $2.6 \times 10^6$ times the original velocity. As a result, the droplet size was reduced to 20 micrometers, as shown in FIG. 9 at a smaller continuous phase flow rate of 10 mL/hr.

Figure 10:
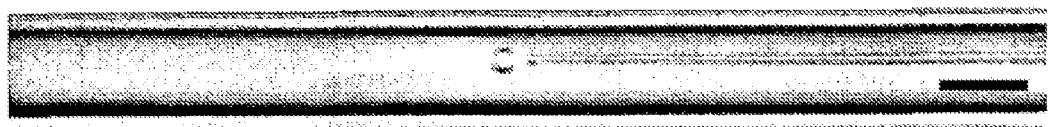
FIG. 10 is a photomicrograph of an emulsion produced using another embodiment of the invention.

FIG. 10 shows the formation of 20 micrometer dodecane droplets in an aqueous solution of 8 mM sodium dodecyl sulfate (SDS) in another microfluidic device incorporating a flow acceleration tube. The flow acceleration tube in this particular example had a diameter of 100 micrometer and the injection tube diameter was 8 micrometers. The flow rate of the aqueous continuous phase used was 10 mL/hr. The scale bar has a length of 100 micrometers.

Figure 11:
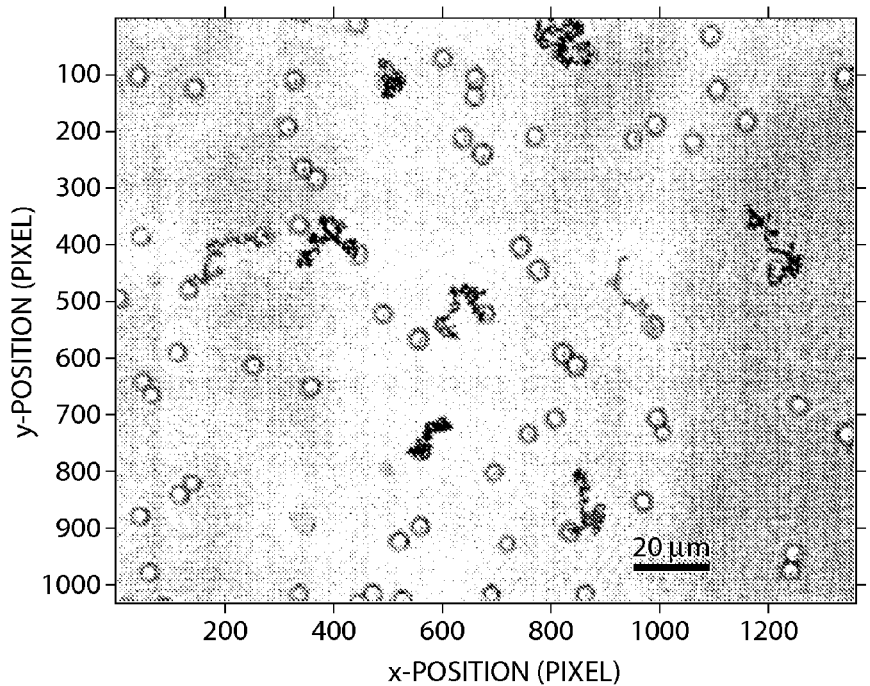
FIG. 11 is a plot illustrating Brownian motion in an emulsion produced in another embodiment of the invention.

In another experiment, using a flow acceleration tube with a diameter of 50 micrometers, octane droplet of 3.8 micrometers in diameter were prepared with a flow rate of the aqueous continuous phase (an aqueous solution of 0.75 wt % sodium dodecyl sulfate (SDS) and 0.25 wt % Tween 80) of 2 mL/hr. As can be seen in FIG. 11, these small octane droplets showed Brownian motion, which is characteristic of small particles suspended in a liquid that results from the random bombardment by the surrounding fluid molecules. In FIG. 11, the various trajectories denote the path walked by the center of the emulsion droplets (not all trajectories are shown in this figure, for clarity).

Figure 12A:
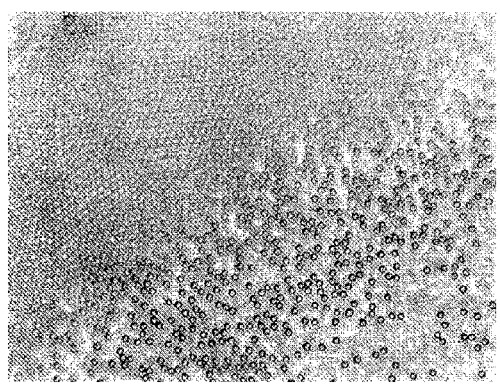
FIG. 12 includes (a) a photomicrograph of an emulsion according to one embodiment of the invention, and (b) a plot of the size distribution of an emulsion according to another embodiment of the invention.
Figure 12B:
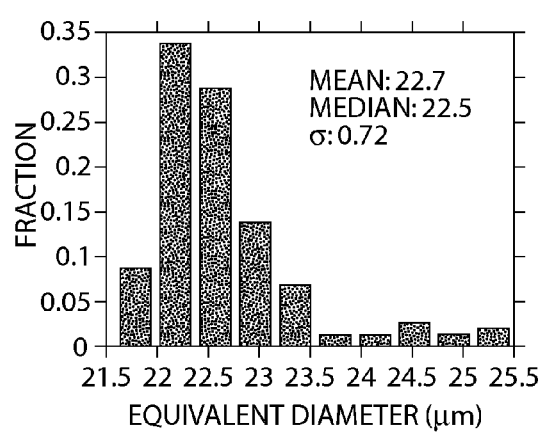

In yet another preliminary experiment, small monodisperse emulsion droplets were used as templates for solid polymer particles. In this experiment, the dispersed phase included a mixture of 2 wt % photoinitiator, Darocur 1173 (2-hydroxy-2-methyl-1-phenyl-1-propanone), and 98 wt % monomer, trimethylolpropane ethoxylate triacrylate. The continuous phase was a mixture of 2% Tween 80, 50% glycerol and 48% water. Upon photo-crosslinking with a bench top ultraviolet light for less than one minute, the emulsion droplets solidified and formed polymer particles. The narrow size distribution of the emulsion droplets was retained after photo-polymerization. This was an effective way of fabricating solid particles on the scale of 3 to 500 micrometers with a narrow size distribution. FIG. 12A illustrates an optical micrograph of the crosslinked polymer particles, while FIG. 12B illustrates the size distribution of the polymer particles, showing a polydispersity of 4% in this example.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
a plurality of outer fluidic droplets, substantially all of the outer fluidic droplets each containing two or more first fluidic droplets each containing one or more second fluidic droplets, wherein each of the plurality of first fluidic droplets contains substantially the same number of second fluidic droplets therein.

2. The article of claim 1, wherein the outer fluid and the first fluid are substantially immiscible.

3. The article of claim 1, wherein the first fluid and second fluid are substantially immiscible.

4. The article of claim 1, wherein the outer fluid and third fluid are substantially miscible.

5. The article of claim 1, wherein substantially all of the outer fluidic droplets each contain three or more first fluidic droplets.

6. The article of claim 1, wherein substantially all of the first fluidic droplets each contain two or more second fluidic droplets.

7. The article of claim 1, wherein substantially all of the first fluidic droplets each contain three or more second fluidic droplets.

8. The article of claim 1, wherein at least about 90% of the outer fluidic droplets each contain two or more first fluidic droplets.

9. The article of claim 1, wherein at least about 90% of the outer fluidic droplets each contain the same number of first fluidic droplets therein.

10. The article of claim 1, wherein at least about 90% of the plurality of first fluidic droplets each contain the same number of second fluidic droplets therein.

11. The article of claim 1, wherein at least some of the second fluidic droplets contain a species therein.

12. The article of claim 11, wherein the species is selected from the group consisting of cells, drugs, nucleic acids, proteins, fragrances, nanoparticles, and quantum dots.

13. The article of claim 11, wherein at least about 90% of the second fluidic droplets each contain the species.

14. An article, comprising:
a plurality of outer fluidic droplets, substantially all of the outer fluidic droplets containing two or more first fluidic droplets each containing two or more second fluidic droplets.

15. The article of claim 14, wherein at least about 90% of the outer fluidic droplets each contain two or more first fluidic droplets.

16. The article of claim 14, wherein at least about 90% of the plurality of outer fluidic droplets each contain the same number of first fluidic droplets therein.

17. The article of claim 14, wherein at least about 90% of the plurality of first fluidic droplets each contain the same number of second fluidic droplets therein.

18. A method of packaging a species comprising:
suspending a species in a first fluid;
flowing the first fluid in a stream surrounded by a second fluid stream, the second fluid being substantially immiscible with the first fluid;
introducing a third fluid stream that surrounds the second fluid stream;
introducing a fourth fluid stream that surrounds the third fluid stream; and
forming multiple droplets of the first fluid, each contained within a second fluidic droplet, the second fluidic droplets contained within a third fluidic droplet contained within the fourth fluid such that substantially all of the third fluidic droplets contain at least two second fluidic droplets, wherein the droplets of the first fluid contain at least one of the species.

19. The method of claim 18, further comprising solidifying a portion of the second fluid surrounding the droplets of the first fluid.

20. The method of claim 18, comprising solidifying at least a portion of the droplets of the first fluid.

* * * * *